(12) United States Patent
Tsai et al.

(10) Patent No.: US 12,384,818 B2
(45) Date of Patent: Aug. 12, 2025

(54) CYCLIN-DEPENDENT KINASE 5 (CDK5) INHIBITORY PEPTIDES

(71) Applicant: Massachusetts Institute of Technology, Cambridge, MA (US)

(72) Inventors: Li-Huei Tsai, Cambridge, MA (US); Jinsoo Seo, Worcester, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 900 days.

(21) Appl. No.: 16/119,656

(22) Filed: Aug. 31, 2018

(65) Prior Publication Data

US 2019/0085029 A1    Mar. 21, 2019

Related U.S. Application Data

(60) Provisional application No. 62/559,824, filed on Sep. 18, 2017.

(51) Int. Cl.
| | |
|---|---|
| *C12N 9/12* | (2006.01) |
| *A61K 38/00* | (2006.01) |
| *A61K 38/03* | (2006.01) |
| *A61K 38/10* | (2006.01) |
| *A61K 38/16* | (2006.01) |
| *A61K 47/60* | (2017.01) |
| *A61K 47/64* | (2017.01) |
| *C07K 7/08* | (2006.01) |

(52) U.S. Cl.
CPC .............. *C07K 7/08* (2013.01); *C12N 9/12* (2013.01); *C12Y 207/11001* (2013.01); *A61K 38/00* (2013.01)

(58) Field of Classification Search
None
See application file for complete search history.

(56) References Cited

U.S. PATENT DOCUMENTS

| | | | |
|---|---|---|---|
| 5,525,727 A | 6/1996 | Bodor | |
| 5,618,803 A | 4/1997 | Bodor | |
| 5,994,055 A * | 11/1999 | Cujec | A61P 31/18 435/5 |
| 6,407,137 B2 | 6/2002 | Shashoua | |
| 6,693,166 B1 | 2/2004 | Wang et al. | |
| 7,119,074 B2 | 10/2006 | Ekwuribe et al. | |
| 9,629,863 B2 | 4/2017 | Ip et al. | |
| 2007/0015183 A1 | 1/2007 | Krainc | |
| 2016/0376333 A1* | 12/2016 | Procko | A61K 39/395 424/130.1 |
| 2017/0121381 A1* | 5/2017 | Offen | C07K 14/4703 |

FOREIGN PATENT DOCUMENTS

| | | |
|---|---|---|
| CN | 102316731 A | 1/2012 |
| CN | 102844323 A | 12/2012 |
| JP | 2012-511583 A | 5/2012 |
| WO | WO-2005035003 A2 * | 4/2005 ........... A61K 31/337 |
| WO | WO 2005/039645 A2 | 5/2005 |
| WO | WO-2006078783 A2 * | 7/2006 ......... C07K 14/4738 |
| WO | WO 2007/047998 A2 | 4/2007 |
| WO | WO-2009012262 A1 * | 1/2009 .............. A61P 25/00 |
| WO | WO 2010/065117 A1 | 6/2010 |
| WO | WO 2010/068692 A | 6/2010 |

OTHER PUBLICATIONS

Kern et al, (Mol Pharmaceutics14: 1450-1459, Mar. 9, 2017).*
Hamley IW, (Biomacromol 15: 1543-1559, 2014).*
Fosgerau et al (Drug Discovery Today 20: 122-128, Jan. 2015).*
Dib et al, PloS One 7: 1-21, 2012 (Abstract only).*
Amini et al., Conditional disruption of calpain in the CNS alters dendrite morphology, impairs LTP, and promotes neuronal survival following injury. J Neurosci. Mar. 27, 2013;33(13):5773-84. doi: 10.1523/JNEUROSCI.4247-12.2013.
Iverson, Interpreting change on the WAIS-III/WMS-III in clinical samples. Arch Clin Neuropsychol. Feb. 2001;16(2):183-91.
Miller et al., Non-aggregating tau phosphorylation by cyclin-dependent kinase 5 contributes to motor neuron degeneration in spinal muscular atrophy. J Neurosci. Apr. 15, 2015;35(15):6038-50. doi: 10.1523/JNEUROSCI.3716-14.2015.
Nguyen et al., Reduction of axonal caliber does not alleviate motor neuron disease caused by mutant superoxide dismutase 1. Proc Natl Acad Sci U S A. Oct. 24, 2000;97(22):12306-11.
Paoletti et al., Dopaminergic and glutamatergic signaling crosstalk in Huntington's disease neurodegeneration: the role of p25/cyclin-dependent kinase 5. J Neurosci. Oct. 1, 2008;28(40):10090-101. doi: 10.1523/JNEUROSCI.3237-08.2008.
Piedrahita et al., Silencing of CDK5 reduces neurofibrillary tangles in transgenic alzheimer's mice. J Neurosci. Oct. 20, 2010;30(42):13966-76. doi: 10.1523/JNEUROSCI.3637-10.2010.
Pollonini et al., Abnormal expression of synaptic proteins and neurotrophin-3 in the Down syndrome mouse model Ts65Dn. Neuroscience. Sep. 22, 2008;156(1):15 pages. Author manuscript. doi: 10.1016/j.neuroscience.2008.07.025. Epub Jul. 25, 2008.
Qu et al., Role of Cdk5-mediated phosphorylation of Prx2 in MPTP toxicity and Parkinson's disease. Neuron. Jul. 5, 2007;55(1):37-52.
Rao et al., Specific calpain inhibition by calpastatin prevents tauopathy and neurodegeneration and restores normal lifespan in tau P301L mice. J Neurosci. Jul. 9, 2014;34(28):9222-34. doi: 10.1523/JNEUROSCI.1132-14.2014.

(Continued)

*Primary Examiner* — Kimberly Ballard
*Assistant Examiner* — Aditi Dutt
(74) *Attorney, Agent, or Firm* — Wolf, Greenfield & Sacks, P.C.

(57) ABSTRACT

The invention relates to methods and compositions for promoting cognitive function and/or treating cognitive function disorders and impairments. In particular the methods are accomplished by administering to a subject a specific CDK5 peptide inhibitor and a pharmaceutically acceptable carrier.

16 Claims, 9 Drawing Sheets

Specification includes a Sequence Listing.

(56) References Cited

OTHER PUBLICATIONS

Seo et al., Activity-dependent p25 generation regulates synaptic plasticity and Aβ-induced cognitive impairment. Cell. Apr. 10, 2014;157(2):486-498. doi:10.1016/j.cell.2014.01.065.
Smith et al., Calpain-regulated p35/cdk5 plays a central role in dopaminergic neuron death through modulation of the transcription factor myocyte enhancer factor 2. J Neurosci. Jan. 11, 2006;26(2):440-7.
Yousuf et al., Involvement of aberrant cyclin-dependent kinase 5/p25 activity in experimental traumatic brain injury. J Neurochem. Jul. 2016;138(2):317-27. doi: 10.1111/jnc.13620. Epub May 25, 2016.
Zhang et al., Diaminothiazoles modify Tau phosphorylation and improve the tauopathy in mouse models. J Biol Chem. Jul. 26, 2013;288(30):22042-56. doi: 10.1074/jbc.M112.436402. Epub Jun. 4, 2013.
International Search Report and Written Opinion for PCT/US2018/049155 mailed Nov. 28, 2018.
International Preliminary Report on Patentability for PCT/US2018/049155 mailed Apr. 2, 2020.
Calcoen et al., What does it take to produce a breakthrough drug? Nat Rev Drug Discov. Mar. 2015;14(3):161-2. doi: 10.1038/nrd4570. PMID: 25722234.
Dehaene et al., Reward-dependent learning in neuronal networks for planning and decision making. Prog Brain Res. 2000;126:217-29. doi: 10.1016/S0079-6123(00)26016-0. PMID: 11105649.
Ershler et al., Novel CDC2-related protein kinases produced in murine hematopoietic stem cells. Gene. Feb. 28, 1993;124(2):305-6. doi: 10.1016/0378-1119(93)90411-u. PMID: 8444355.
Fray et al., CANTAB battery: proposed utility in neurotoxicology. Neurotoxicol Teratol. Jul.-Aug. 1996;18(4):499-504. doi: 10.1016/0892-0362(96)00027-x. PMID: 8866544.
Langer, New methods of drug delivery. Science. Sep. 28, 1990;249(4976):1527-33. doi: 10.1126/science.2218494. PMID: 2218494.
Moorthamer et al., Identification of a human cDNA encoding a kinase-defective cdk5 isoform. Biochem Biophys Res Commun. Dec. 18, 1998;253(2):305-10. doi: 10.1006/bbrc.1998.9737. PMID: 9878533.
Patrick et al., Conversion of p35 to p25 deregulates Cdk5 activity and promotes neurodegeneration. Nature. Dec. 9, 1999;402(6762):615-22. doi: 10.1038/45159. PMID: 10604467.
Takahashi et al., Cyclin-dependent kinase 5 (Cdk5) associated with Lewy bodies in diffuse Lewy body disease. Brain Res. Apr. 17, 2000;862(1-2):253-6. doi: 10.1016/s0006-8993(00)02086-2. PMID: 10799694.
Tarricone et al., Structure and regulation of the CDK5-p25(nck5a) complex. Mol Cell. Sep. 2001;8(3):657-69. doi: 10.1016/s1097-2765(01)00343-4. PMID: 11583627.
Wang et al., Cdk5 activation induces hippocampal CA1 cell death by directly phosphorylating NMDA receptors. Nat Neurosci. Oct. 2003;6(10):1039-47. doi: 10.1038/nn1119. Epub Sep. 21, 2003. PMID: 14502288.
Weaver et al., Mild memory impairment in healthy older adults is distinct from normal aging. Brain Cogn. Mar. 2006;60(2):146-55. doi: 10.1016/j.bandc.2005.10.004. Epub Jan. 30, 2006. PMID: 16446021.
Terada, The chemistry of enzymes. <https://web.archive.org/web/20070901031543/http://www.sc.fukuoka-u.ac.jp:80/~bc1/Biochem/biochem.htm>.
International Search Report and Written Opinion mailed Nov. 28, 2018, for Application No. PCT/US2018/049155.
International Preliminary Report on Patentability mailed Apr. 2, 2020, for Application No. PCT/US2018/049155.
Ershler et al., Novel CDC2-related protein kinases produced in murine hematopoietic stem cells. Gene. Feb. 28, 1993;124(2):305-6.
Moorthamer et al., Identification of a human cDNA encoding a kinase-defective cdk5 isoform. Biochem Biophys Res Commun. Dec. 18, 1998;253(2):305-10.
Shukla et al., A truncated peptide from p35, a Cdk5 activator, prevents Alzheimer's disease phenotypes in model mice. FASEB J. Jan. 2013;27(1):174-86. doi: 10.1096/fj.12-217497. Epub Oct. 4, 2012.
Tarricone et al., Structure and regulation of the CDK5-p25(nck5a) complex. Mol Cell. Sep. 2001;8(3):657-69.
Chai et al., Genomic organization and promoter cloning of the human X11α gene APBA1. DNA Cell Biol. May 2012;31(5):651-9. doi: 10.1089/dna.2011.1447. Epub Dec. 2, 2011.
Sun et al., The transcriptional repressor Sp3 is associated with CK2-phosphorylated histone deacetylase 2. J Biol Chem. Sep. 27, 2002;277(39):35783-6. Epub Aug. 9, 2002.
Wagner et al., Kinetically Selective Inhibitors of Histone Deacetylase 2 (HDAC2) as Cognition Enhancers. Chem Sci. Jan. 1, 2015;6(1):804-815.
Shukla et al., TFP5, a Peptide Inhibitor of Aberrant and Hyperactive Cdk5/p25, Attenuates Pathological Phenotypes and Restores Synaptic Function in CK-p25Tg Mice. J Alzheimer's Dis. 2017;56(1):335-349. doi: 10.3233/JAD-160916.

* cited by examiner

The sequence of CdkS inhibitory (CdkSi) peptide

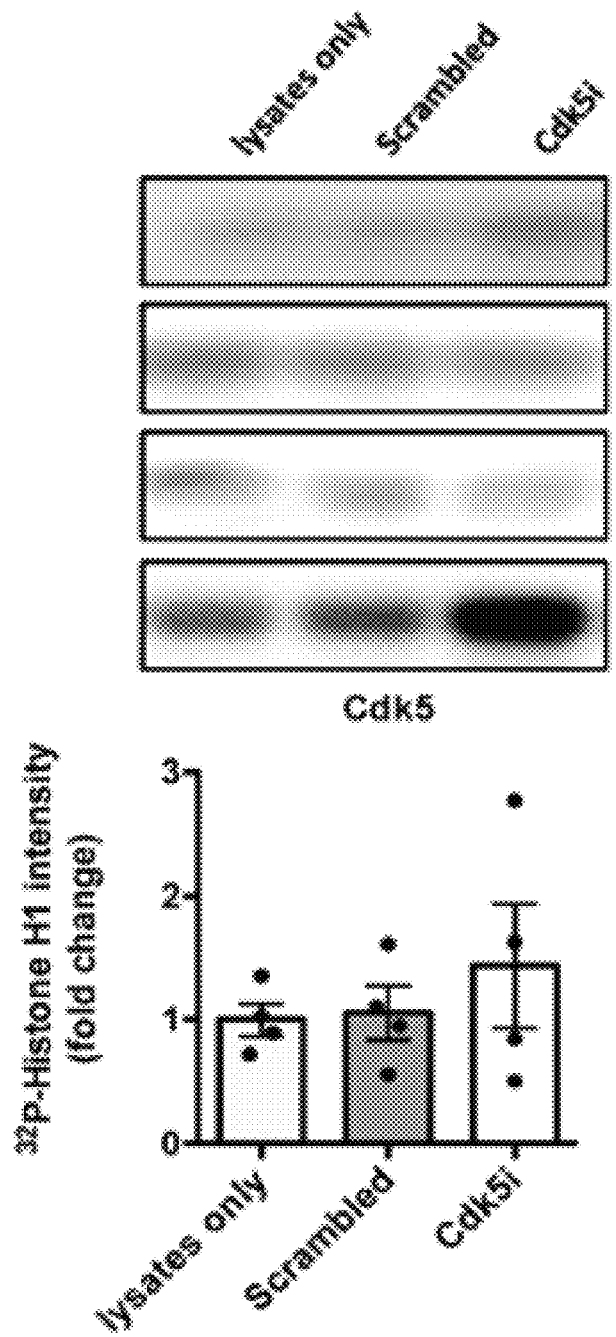

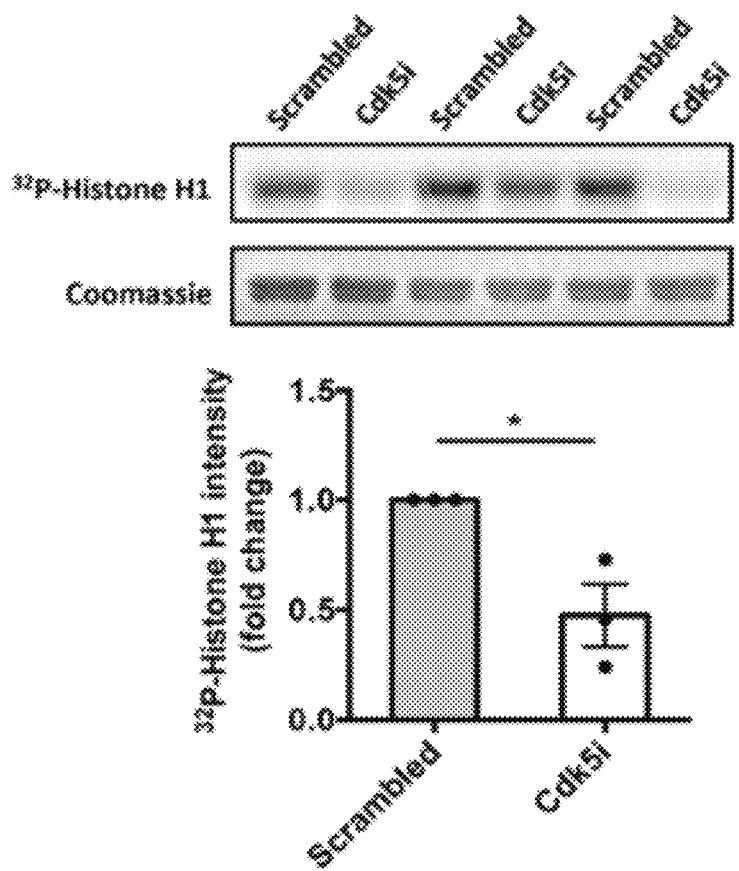

Fig. 9
9A FITC-Ahx-ARAFGIPVRCYSYGRKKRRQRRR (SEQ ID NO. 3)
Cdk5i peptide    TAT
9B Hoechst 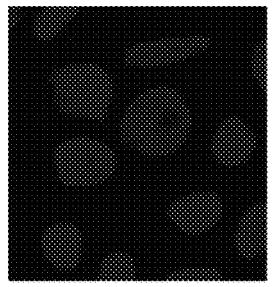  FITC 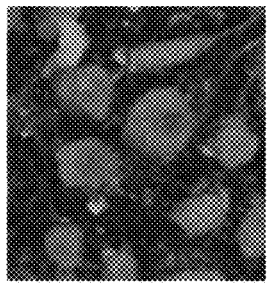  Merge (combined Hoechst and FITC) 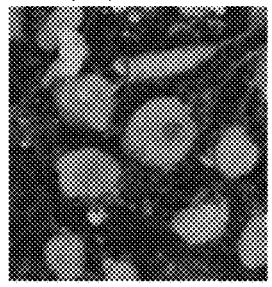

CYCLIN-DEPENDENT KINASE 5 (CDK5) INHIBITORY PEPTIDES

RELATED APPLICATION

This application claims priority under 35 U.S.C. 119(e) to U.S. provisional patent application, U.S. Ser. No. 62/559,824, filed. Sep. 18, 2017, which is incorporated herein by reference in its entirety.

GOVERNMENT SUPPORT

This invention was made with Government support under Grant No. R37 NS051874 awarded by the National Institutes of Health. The Government has certain rights in the invention.

BACKGROUND OF THE INVENTION

Brain atrophy occurs during normal aging and is an early feature of neurodegenerative diseases associated with impaired cognitive function and memory loss. Alzheimer's disease. Huntington's disease, frontotemporal dementia, and other related dementias cause marked loss in cognitive function, often reducing an afflicted person to an invalid state. No cure is known for Alzheimer's disease and related dementias, and the causes of these diseases are not well understood. Moreover, pre-clinical research has not yet explored strategies to recover lost memories after substantial neuronal loss has taken place.

Cyclin-dependent kinase 5 (CDK5), a tau kinase and member of the CDK family, plays multiple roles in brain development and has been implicated in a number of neurodegenerative diseases. Specifically, CDK5, a proline-directed serine/threonine kinase, is activated by p25 protein. This occurs as intracellular levels of calcium rise, activating calpain, which then cleaves p35 into p25, and p25 then binds with CDK5. p25, unlike p35, is not readily degraded and its binding to CDK5 constitutively activates CDK5, leading to hyperphosphorylation of tau. Deregulation of CDK5 activity has been shown to result in neuronal death, elevated amyloid β (Aβ) accumulation, reduced synaptic plasticity, cytoskeletal disruption, morphological degeneration, apoptosis, and impaired learning.

SUMMARY OF THE INVENTION

The invention relates, in one aspect, to the discovery of methods and compositions for promoting cognitive function and thus for the treatment of memory loss and cognitive function disorders/impairments. Accordingly, one aspect of the invention involves methods of treating cognitive function disorders or impairments in a subject in need thereof. The methods comprise administering to the subject a cyclin-dependent kinase 5 inhibitory (CDK5i) peptide and a pharmaceutically acceptable carrier.

The invention in one aspect is a pharmaceutical composition, comprising a peptide of 5-50 amino acids in length having at least 50% amino acid sequence identity over its length relative to the amino acid sequence of SEQ ID NO: 1 having the following structure: ARAFGX$_1$PVRC X$_2$S* (X$_1$=I or V and X$_2$=Y or F) and a pharmaceutically acceptable carrier.

In some embodiments, the peptide comprises SEQ ID NO: 2. In one embodiment, the peptide comprises at least one conservative substitution within the sequence of SEQ ID NO: 1.

In some embodiments, the pharmaceutically acceptable carrier comprises a polymer. In one embodiment, the polymer comprises a hydrophilic block and an endosomolytic block. In another embodiment, the hydrophilic block comprises polyethylene glycol methacrylate, and wherein the endosomolytic block comprises a diethylaminoethyl methacrylate-butyl methacrylate copolymer. In some embodiments, the polymer is a stimuli-responsive polymer that responds to one or more stimuli selected from the group consisting of pH, temperature, UV-visible light, photo-irradiation, exposure to an electric field, ionic strength, and the concentration of certain chemicals by exhibiting a property change.

In some embodiments, the peptide has a deletion of 1 to 2 amino acids of SEQ ID NO: 1. In one embodiment, the peptide comprises at least 1 additional amino acid at the N terminus of SEQ ID NO: 1. In another embodiment, the peptide comprises at least 1 additional amino acid at the C terminus of SEQ ID NO: 1.

In some embodiments, the peptide is linked to a non-peptide molecule through a linker. In one embodiment, the non-peptide molecule is a PEG or TEG.

In some embodiments, the peptide has a reinforced or stabilized secondary structure.

The invention, in another aspect is a peptide consisting essentially of 5-25 amino acids in length having at least 50% amino acid sequence identity over its length relative to the amino acid sequence of SEQ ID NO: 1 having the following structure: ARAFGX$_1$PVRC X$_2$S*(X$_1$=I or V and X$_2$=Y or F).

In some embodiments, the peptide comprises at least one conservative substitution. In one embodiment, the peptide has at least 60%, 70%, 80%, 90% or 95% amino acid sequence identity over its length relative to the amino acid sequence of SEQ ID NO: 1. In another embodiment, the peptide comprises at least one conservative substitution within the sequence of SEQ ID NO: 1. In some embodiments, the peptide has a deletion of 1 to 2 amino acids of SEQ ID NO: 1. In one embodiment, the peptide comprises at least 1 additional amino acid at the N terminus of SEQ ID NO: 1. In another embodiment, the peptide comprises at least 1 additional amino acid at the C terminus of SEQ ID NO: 1.

In some embodiments, the peptide is linked to a non-peptide molecule through a linker. In one embodiment, the non-peptide molecule is a PEG or TEG. In another embodiment, the peptide has a reinforced or stabilized secondary structure.

The invention, in another aspect, is a peptide comprising the amino acid sequence of SEQ ID NO: 1 having the following structure: ARAFGX$_1$PVRC X$_2$S*(X$_1$=I or V and X$_2$=Y or F), wherein the peptide is 12-50 amino acids in length.

The disclosure, in another aspect, provides a recombinant nucleic acid encoding any one of the peptides described above. Another aspect of the disclosure includes a recombinant expression vector comprising the nucleic acid described above operatively linked to a promoter. A further aspect of the disclosure provides a recombinant host cell comprising the recombinant expression vector described above.

The invention, in another aspect, provides a method for treating a neurodegenerative condition in a subject, comprising administering to the subject a specific CDK5 peptide inhibitor, or nucleic acid encoding the peptide inhibitor, that disrupts a CDK5-p25/p35 interaction without disrupting CDK5 basal activity or interacting with CDK1 or CDK2.

In some embodiments, the subject also undergoes an additional therapy to treat the disorder. In another embodiment, the specific CDK5 peptide inhibitor is administered orally, transdermally, intravenously, cutaneously, subcutaneously, nasally, intramuscularly, intraperitoneally, intracranially, or intracerebroventricularly.

In some embodiments, the neurodegenerative condition is Alzheimer's disease, Huntington's disease, frontotemporal dementia, seizure-induced memory loss, schizophrenia, Rubinstein Taybi syndrome, Rett Syndrome, Fragile X, Lewy body dementia, vascular dementia, ADHD, dyslexia, bipolar disorder and social, cognitive and learning disorders associated with autism, traumatic head injury, or attention deficit disorder. In other embodiments, the cognitive function disorders/impairments are associated with anxiety disorders, conditioned fear response, panic disorders, obsessive compulsive disorders, post-traumatic stress disorder, phobias, social anxiety disorders, or substance dependence recovery.

In some embodiments, the method further comprises exposing the subject to cognitive behavioral therapy (CBT), psychotherapy, behavioral exposure treatments, virtual reality exposure (VRE) or cognitive remediation therapy. In one embodiment, the CDK5 peptide inhibitor is administered once a day, every other day, every third day, every fourth day, every fifth day, every sixth day, or every seventh day.

In some embodiments, the peptide comprises 5-50 amino acids in length having at least 50% amino acid sequence identity over its length relative to the amino acid sequence of SEQ ID NO: 1 having the following structure: ARAFGX$_1$PVRC X$_2$S*(X$_1$=I or V and X$_2$=Y or F).

In some embodiments, the peptide comprises at least one conservative substitution. In other embodiments, the peptide has at least 60%, 70%, 80%, 90% or 95% amino acid sequence identity over its length relative to the amino acid sequence of SEQ ID NO: 1. In another embodiment, the peptide comprises at least one conservative substitution within the sequence of SEQ ID NO: 1. In some embodiments, the peptide has a deletion of 1 to 2 amino acids of SEQ ID NO: 1. In another embodiment, the peptide comprises at least 1 additional amino acid at the N terminus of SEQ ID NO: 1. In other embodiments, the peptide comprises at least 1 additional amino acid at the C terminus of SEQ ID NO: 1.

In some embodiments, the peptide is linked to a non-peptide molecule through a linker. In one embodiment, the non-peptide molecule is a PEG or TEG. In another embodiment, the peptide has a reinforced or stabilized secondary structure.

In some embodiments, the peptide has a length of 8-25 amino acids. In another embodiment, the peptide has a length of 8-20 amino acids. In other embodiments, the peptide has a length of 10-15 amino acids.

Each of the limitations of the invention can encompass various embodiments of the invention. It is, therefore, anticipated that each of the limitations of the invention involving any one element or combinations of elements can be included in each aspect of the invention. This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing", "involving", and variations thereof herein, is meant to encompass the items listed thereafter and equivalents thereof as well as additional items.

BRIEF DESCRIPTION OF DRAWINGS

The figures are illustrative only and are not required for enablement of the invention disclosed herein.

FIG. 1A shows the structure of a p25/CDK5 complex. FIG. 1B shows the sequence of exemplary CDK5 inhibitory peptides. The sequences, from top to bottom, correspond to SEQ ID NOs: 5-13. The sequence of the CDK5 inhibitory peptide (boxed in the first row), is SEQ NO: 2.

FIGS. 5A-5B show some of CDK5i peptide's effects: in FIG. 5A, CDK5i peptide is shown to not affect basal CDK5 activity, whereas FIG. 5B shows that CDK5i peptide significantly reduces of CDK5 activity in brain from P301S mice.

FIG. 9A shows SEQ ID No. 3 linked at the N-terminus to a fluorescein isothiocyanate (FITC) with a linker (aminohexanoic acid; Ahx) for visualization studies.

FIG. 9B shows the results of human iPSC-derived neural progenitor cells that were treated with FITC-Ahx-Cdk5i-Tat (1 μM) (SEQ ID NO. 3) for 2 hr and subjected to imaging.

DETAILED DESCRIPTION

Figures 1A, 1B:
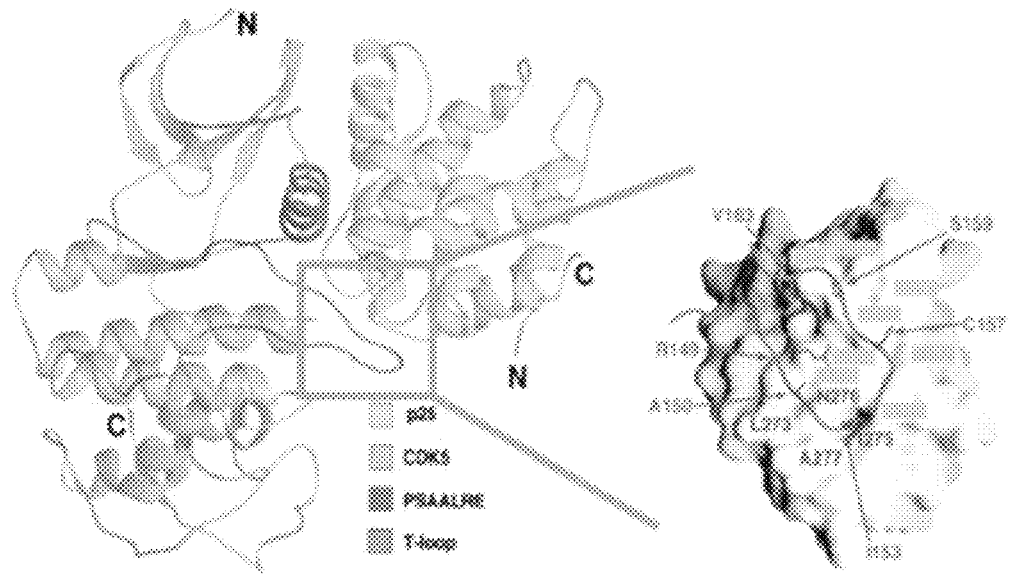
FIGS. 1A-1B show details of the p25/CDK5 complex and CDK5 inhibitory peptide.

The invention relates, in one aspect, to the discovery of methods and compositions for the treatment of neurodegenerative disorders. For instance, the compounds of the invention are useful for promoting cognitive function and thus for the treatment of memory loss and cognitive function disorders/impairments. Accordingly, one aspect of the invention involves methods of treating cognitive function disorders/impairments by administering to a subject in need thereof an effective amount of a CDK5 peptide inhibitor.

Surprisingly it has been discovered according to the invention that the CDK5 peptide inhibitors selectively block the interaction of CDK5 with p25/p35, without affecting basal CDK5 activity or interacting with other CDKs having high homology to CDK5. This is in stark contrast to drugs that have been used to inhibit CDK5 hyperactivity, as they have shown poor specificity and affect the activity of other CDKs. Consequently, prior art CDK5 inhibitors inhibit basal CDK5 activity under normal conditions, possibly causing abnormal neuronal function, leading to serious side effects.

The CDK5 peptide inhibitors of the invention demonstrate high specificity, thus avoiding serious side effects associated with disrupting basal CDK5 activity. Additionally it was demonstrated that the peptides are capable of crossing the blood brain barrier.

As shown in the Examples below, peptides that disrupt the binding of CDK5 and p25/p35 by interacting at a specific region with one or more of these proteins, have significant therapeutic properties. The disruption prevents the complex formation, thus avoiding the downstream effects of CDK5/p25 complexation such as neuronal death, elevated amyloid β (Aβ) accumulation, reduced synaptic plasticity, cytoskeletal disruption, morphological degeneration, apoptosis, and impaired learning. While disrupting the specific complex formation, the peptide inhibitors described herein avoid side effects associated with non-specific binding to structurally similar molecules. For instance, it was shown in the Examples provided herein that peptides can be designed to specifically inhibit CDK5 binding to p25/p35. It was determined that a CDK5 peptide inhibitor such as CDK5 inhibitory (CDK5i) peptide of SEQ ID NO: 2 would interrupt the formation of the p25/CDK5 complex, as the CDK5 peptide inhibitor would interact with both CDK5 and p25. In vitro testing showed that a CDK5 peptide inhibitor significantly reduced CDK5 kinase activity compared to a scrambled peptide control. Using a mouse model of the neurodegenerative brain, it was found that, while the CDK5 peptide inhibitor interacted with both CDK5 and p35 (a precursor of p25), it did not bind to CDK1 or CDK2, which are highly homologous to CDK5. Further, it was surprisingly found that the CDK5 peptide inhibitor did not affect basal CDK5 activity in control mice, but did significantly reduce kinase activity of CDK5 in the brain of an Alzheimer's disease (AD) and frontotemporal dementia (FTD) mouse model (P301S mice). These findings demonstrate that the peptide inhibitors of the invention provide valuable therapeutic effects.

Further, a human AD-related pathology model system was employed using induced-pluripotent stem cells (iPSCs) created from fibroblasts of familiar AD (fAD) patients. Neural progenitor cells (NPCs) derived from fAD iPSCs showed a number of pathological phenotypes, including upregulation of historic deacetylase 2 (HDAC2, which negatively regulates the transcription of genes associated with learning and memory); however, NPCs treated with a CDK5 peptide inhibitor showed significantly reduced levels of HDAC2 and γH2AX signaling (indicative of DNA damage) compared to a scrambled peptide. Thus, some methods of the invention comprise administering a CDK5 peptide inhibitor described herein, to a subject in need thereof.

The compositions of the invention include cyclin-dependent kinase 5 (CDK5) peptide inhibitors, which may be used to treat neurodegenerative disorders.

Cyclin-dependent kinase 5 (CDK5) has been implicated in numerous pathological phenotypes in neurodegenerative disorders. Pharmacological inhibition or targeted knockdown of CDK5 has been shown to relieve neurotoxicity and tau pathology in selected neurodegenerative disorders, including Alzheimer's disease, Parkinson's disease, spinal muscular atrophy, and frontotemporal dementia (Qu et al., 2007; Piedrahita et al., 2010; Zhang et al., 2013; Miller et al., 2015). The aberrant CDK5 activity under pathological conditions is mediated by p25, a proteolytic fragment of p25, which has been shown to induce various pathological phenotypes, such as neuroinflammation, hyperphosphorylation of tau, and neuronal death in the neurodegenerative brain. Inhibition of the p25/CDK5 complex has been shown to be beneficial in the diseased state; for example, in 5×FAD mice an Alzheimer's disease mouse model), blockade of p25 generation reduces the formation of amyloid plaques and attenuates Aβ-induced synaptic depression, glial activation, neuroinflammation, and neuronal death (Amini et al., 2013; Rao et al., 2014; Seo et al., 2014). Blockade of p25 was also shown in restore synaptic plasticity and cognitive performance of the AD mice (Seo et al., 2014).

The CDK5 peptide inhibitor of the present invention is a peptide that interacts with the binding regions of CDK5 and p25 and interrupts the formation of the CDK5/p25 complex. The binding of the CDK5 peptide inhibitor is specific in that the peptide does not significantly affect related effectors or pathways such as basal CDK5 activity or CDK1 or CDK2. A peptide is considered to not significantly affect basal CDK5 activity when basal CDK5 activity remains substantially similar before and after exposure to the CDK5 peptide inhibitor. A level of basal CDK5 activity can be assessed by in vitro or in vivo assays. A level of basal CDK5 activity that remains substantially similar may be within 10%, 5%, 4%, 3%, 2%, or 1% of pre-exposure levels.

A peptide is considered to not significantly affect CDK1 or CDK2 binding when significant levels of the peptide do not bind to CDK1 and/or CDK2 after exposure to the CDK5 peptide inhibitor. A level of binding can be assessed by in vitro or in vivo assays known to the skilled artisans, including the assay presented in the examples section below. A level of binding of the peptide inhibitor to CDK1 and/or CDK2 that is considered to be insignificant may be less than or equal to 10%, 5%, 4%, 3%, 2%, or 1% of bound complex within a mixture of CDK5 peptide inhibitor and CDK1 and/or CDK2.

The length of the CDK5 peptide inhibitors may vary. For example, the CDK5 peptide inhibitors may be 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 amino acids long. In select embodiments, the CDK5 peptide inhibitor is 8-20, 10-20, 8-15, 10-15, 8-12, 10-12 or 12 amino acids long. A peptide having such a short peptide chain has a high structural stability (for example, resistance to protease) and has excellent handling properties and storage properties.

In some embodiments, the CDK5 peptide inhibitor is a peptide comprising an amino acid sequence having at least 50% amino acid sequence identity over its length relative to the amino acid sequence of the following sequence: ARAFGX$_1$PVRCX$_2$S*(X$_1$=I or V and X$_2$=Y or F) (SEQ ID NO: 1). In some embodiments, the CDK5 peptide inhibitor has 50-100% (i.e., 50-60%, 50-70%, 50-80%, 50-90%, 60-70%, 60-80%, 60-90%, 60-100%, 70-80%, 70-90%, 70-100%, 80-90%, 80-100%, or 90-100%) sequence identity to the amino acid sequence set forth in SEQ ID NO: 1. For example, the CDK5 peptide inhibitor may have greater than 80%, 85%, 90%, 91%, 92%, 93%, 94%, 95%, 96%, 97%, 98%, 99%, or 100% sequence identity to the amino acid sequence set forth in SEQ ID NO: 1.

In one particular embodiment, CDK5 peptide inhibitor is a peptide comprising an amino acid sequence having at least 50% amino acid sequence identity over its length relative to the amino acid sequence of ARAFGIPVRCYS (SEQ ID NO: 2; FIG. 1B). In some embodiments, the CDK5 peptide inhibitor has 50-100% (i.e., 50-60%, 50-70%, 50-80%, 50-90%, 60-70%, 60-80%, 60-90%, 60-100%, 70-80%, 70-90%, 70-100%, 80-90%, 80-100%, or 90-100%) sequence identity to the amino acid sequence set forth in SEQ ID NO: 2. For example, the CDK5 peptide inhibitor may have greater than 80%, 85%, 90%, 91%, 92%, 93%, 94%, 95%, 96%, 97%, 98%, 99%, or 100% sequence identity to the amino acid sequence set forth in SEQ ID NO: 2.

The peptides disclosed herein may be modified through the addition of one or more components at either end of the peptide. For instance, the peptides may be modified to add a label such as FITC at the C-terminus and/or N-terminus, with or without a linker, such as aminohexanoic acid; Ahx. The peptides may also include a functional component at either or both ends of the peptide. For instance a functional component may include a targeting peptide or domain, such as an antibody or antibody fragment, a translocation peptide or domain such as a Transactivator of transcription (TAT) peptide or a stabilization peptide or domain, with or without a linker. An exemplary modified peptide is ARAF-GIPVRCYSYGRKKRRQRRR (SEQ ID NO. 3), which includes a Cdk5i peptide (ARAFGIPVRCYS) (SEQ ID NO: 2) linked directly to a HIV TAT peptide (YGRKKRRQRRR) (SEQ ID NO: 4).

In one particular embodiment, CDK5 peptide inhibitor is a peptide comprising an amino acid sequence having at least 50% amino acid sequence identity over its length relative to the amino acid sequence of ARAF-GIPVRCYSYGRKKRRQRRR (SEQ ID NO. 3–SEQ ID No: 2+YGRKKRRQRRR (SEQ ID NO: 4)). In some embodiments, the CDK5 peptide inhibitor has 50-100% (i.e., 50-60%, 50-70%, 50-80%, 50-90%, 60-70%, 60-80%, 60-90%, 60-100%, 70-80%, 70-90%, 70-100%, 80-90%, 80-100%, or 90-100%) sequence identity to the amino acid sequence set forth in SEQ ID NO: 3. For example, the CDK5 peptide inhibitor may have greater than 80%, 85%, 90%, 91%, 92%, 93%, 94%, 95%, 96%, 97%, 98%, 99%, or 100% sequence identity to the amino acid sequence set forth in SEQ ID NO: 3.

A "translocation peptide" or "translocation domain" refers to any sequence of amino acids that directs a peptide in which it is present to a desired cellular destination. For example a translocation domain such as a polyarginine sequence can direct or facilitate penetration of the peptide across a biological membrane, e.g., a phospholipid membrane, mitochondrial membrane, or nuclear membrane. For example the translocation sequence directs the peptide from outside the cell, through the plasma membrane, and into the cytoplasm or to a desired location within the cell, e.g., the nucleus, the ribosome, the mitochondria, the ER, a lysosome, or peroxisome. Alternatively, or in addition, the translocation sequence can direct the peptide across a physiological barrier such as the blood-brain barrier, the transmucosal barrier, or the hematoencephalic, hematoretinal, gastrointestinal and pulmonary barriers.

The CDK5 peptide inhibitors described herein are not naturally occurring peptides. Most of the peptides have non-naturally occurring sequences where one or more amino acids differ from a naturally occurring sequence. In some embodiments the CDK5 peptide inhibitor includes one or more amino acids that is not included within the full CDK5 polypeptide. In the instance where the peptide has an amino acid sequence (SEQ ID NO: 2) that forms a portion of a naturally occurring polypeptide (full CDK5) the peptide itself is not naturally occurring because it is less than the whole peptide. Not all peptide fragments of the full CDK5 polypeptide are CDK5 peptide inhibitors of the invention because they do not specifically disrupt CDK5 and p25/p35 binding.

The peptide may be 8 amino acids in length or it may be longer. For instance, the peptide may have additional amino acids at the N and/or C terminus. The amino acids at either terminus may be anywhere between 1 and 100 amino acids. In some embodiments the peptide includes 1-50, 1-20, 1-15, 1-10, 1-5 or any integer range there between.

The peptide may be cyclic or non-cyclic. Cyclic peptides in some instances have improved stability properties. Those of skill in the art know how to produce cyclic peptides.

The peptides of the invention may include conservative substitutions. As used herein, "conservative amino acid substitution" means amino acid or nucleic acid substitutions that do not alter or substantially alter peptide or polynucleotide function or other characteristics. A given amino acid can be replaced by a residue having similar physiochemical characteristics, e.g., substituting one aliphatic residue for another (such as Ile, Val, Leu, or Ala for one another), or substitution of one polar residue for another (such as between Lys and Arg; Glu and Asp; or Gln and Asn). Other such conservative substitutions, e.g., substitutions of entire regions having similar hydrophobicity characteristics, are well known. Peptides comprising conservative amino acid substitutions can be tested in any one of the assays described herein to confirm that a desired activity is retained.

Amino acids can be grouped according to similarities in the properties of their side chains: (1) non-polar: Ala (A), Val (V), Leu (L), Ile (I), Pro (P), Phe (F), Trp (W), Met (M); (2) uncharged polar: Gly (G), Ser (S), Thr (T), Cys (C), Tyr (Y), Asn (N), Gln (Q); (3) acidic: Asp (D), Glu (E); (4) basic: Lys (K), Arg (R), His (H). Alternatively, naturally occurring residues can be divided into groups based on common side-chain properties: (1) hydrophobic: Norleucine, Met, Ala, Val, Leu, Ile; (2) neutral hydrophilic: Cys, Ser, Thr, Asn, Gln; (3) acidic: Asp, Glu; (4) basic: His, Lys, Arg; (5) residues that influence chain orientation: Gly, Pro; (6) aromatic: Trp, Tyr, Phe. Non-conservative substitutions will entail exchanging a member of one of these classes for another class. Particular conservative substitutions include, for example, Ala into Gly or into Ser; Arg into Lys; Asn into Gln or into H is; Asp into Glu; Cys into Ser; Gln into Asn; Gln into Asp; Gly into Ala or into Pro; His into Asn or into Gln; Ile into Leu or into Val; Leu into Ile or into Val; Lys into Arg, into Gln or into Glu; Met into Leu, into Tyr or into Ile; Phe into Met, into Leu or into Tyr; Ser into Thr; Thr into Ser; Trp into Tyr; Tyr into Trp; and/or Phe into Val, into Ile or into Leu.

As used throughout the present application, the term "peptide" is used in its broadest sense to refer to a sequence of subunit amino acids. The peptides of the invention may comprise L-amino acids, D-amino acids (which are resistant to L-amino acid-specific proteases in vivo), or a combination of D- and L-amino acids. The peptides described herein may be chemically synthesized or recombinantly expressed. The peptides may be linked to other compounds to promote an increased half-life in vivo, such as by PEGylation, HESylation, PASylation, glycosylation, or may be produced as an Fc-fusion or in deimmunized variants. Such linkage can be covalent or non-covalent as is understood by those of skill in the art.

The peptides may also be linked to other molecules. The peptide and molecule may be linked directly to one another (e.g., via a peptide bond); linked via a linker molecule, which may or may not be a peptide; or linked indirectly to one another by linkage to a common carrier molecule, for instance.

Thus, linker molecules ("linkers") may optionally be used to link the peptide to another molecule. Linkers may be peptides, which consist of one to multiple amino acids, or non-peptide molecules. Examples of peptide linker molecules useful in the invention include glycine-rich peptide linkers, wherein more than half of the amino acid residues are glycine. Preferably, such glycine-rich peptide linkers consist of about 20 or fewer amino acids.

In some embodiments a linker is composed of glycine and serine. For instance the linker may be Gly-Ser, or Gly-Gly-Ser. Alternatively it may be either of those sequences with 1-4 Gly on one or both ends and/or 1-2 Ser on either ends. A sequence comprising 2-10 or 2-5 consecutively linked copies of any one of those amino acid sequences may be employed as a peptide linker.

In another aspect of the invention, peptides are covalently bound to a polyethylene glycol (PEG) molecule by their C-terminal terminus or a lysine residue, notably a PEG of 1500 or 4000 MW, for a decrease in urinary clearance and in therapeutic doses used and for an increase of the half-life in blood plasma. In yet another embodiment, peptide half-life is increased by including the peptide in a biodegradable and biocompatible polymer material for drug delivery system forming microspheres. Polymers and copolymers are, for instance, poly(D,L-lactide-co-glycolide) (PLGA). The peptide for instance, may be linked to a PEG or TEG molecule. Such a molecule is referred to as a PEGylated or TEGylated peptide.

A peptide may be derived from SEQ ID NO: 1 or 2 by any chemical modification that improves its resistance to proteolysis; and a substantially homologous peptide may be derived from SEQ ID NO: 1 or 2 by substitution of one or more amino acids. By "substituted" or "modified" the present invention includes those amino acids that have been altered or modified from naturally occurring amino acids.

In particular, the N- and/or C-terminus of the peptides described herein may be optionally protected against proteolysis. For instance, the N-terminus may be in the form of an acetyl group, and/or the C-terminus may be in the form of an amide group. Internal modifications of the peptides to be resistant to proteolysis are also envisioned, e.g. wherein at least a —CONH— peptide bond is modified and replaced by a (CH$_2$NH) reduced bond, a (NHCO) retro-inverso bond, a (CH$_2$—O) methylene-oxy bond, a (CH$_2$—S) thiomethylene bond, a (CH$_2$CH$_2$) carba bond, a (CO—CH$_2$) cetomethylene bond, a (CHOH—CH$_2$) hydroxyethylene bond), a (N—N) bound, a E-alcene bond or also a —CH=CH— bond.

For instance the peptide may be modified by acetylation, acylation, amidation, crosslinking, cyclization, disulfide bond formation, formation of covalent cross-links, formation of cysteine, formation of pyroglutamate, formylation, gamma-carboxylation, glycosylation, GPI anchor formation, hydroxylation, iodination, methylation, myristylation, oxidation, phosphorylation, and the like.

The peptides of the invention may be composed of amino acid(s) in D configuration, which render the peptides resistant to proteolysis. They may also be stabilized by intramolecular crosslinking, e.g. by modifying at least two amino acid residues with olefinic side chains, preferably C3-C8 alkenyl chains, preferably penten-2-yl chains, followed by chemical crosslinking of the chains, according to the so-called "staple" technology. For instance, amino acids at position i and i+4 to i+7 can be substituted by non-natural amino acids that show reactive olefinic residues. All these proteolysis-resistant chemically-modified peptides are encompassed in the present invention. Two amino acid sequences are "homologous", "substantially homologous" or "substantially similar" when one or more amino acid residue are replaced by a biologically similar residue or when greater than 80% of the amino acids are identical, or greater than about 90%, preferably greater than about 95%, are similar (functionally identical).

Preferably, the similar or homologous sequences are identified by alignment using, for example, the GCG (Genetics Computer Group, Program Manual for the GCG Package, Version 7, Madison, Wis.) pileup program, or any of the programs known in the art (BLAST, FASTA, etc.).

Peptides described herein can be synthesized using standard synthetic methods known to those skilled in the art, for example chemical synthesis or genetic recombination. In a preferred embodiment, peptides are obtained by stepwise condensation of amino acid residues, either by condensation of a preformed fragment already containing an amino acid sequence in appropriate order, or by condensation of several fragments previously prepared, while protecting the amino acid functional groups except those involved in peptide bond during condensation. In particular, the peptides can be synthesized according to the method originally described by Merrifield.

In some instances, peptides can include only natural amino acids, although non-natural amino acids (i.e., compounds that do not occur in nature but that can be incorporated into a peptide chain) and/or amino acid analogs as are known in the art may alternatively be employed.

There are many known unnatural amino acids any of which may be included in the peptides of the present invention. Some examples of unnatural amino acids are 4-hydroxyproline, desmosine, gamma-aminobutyric acid, beta-cyanoalanine, norvaline, 4-(E)-butenyl-4(R)-methyl-N-methyl-L-threonine, N-methyl-L-leucine, 1-amino-cyclopropanecarboxylic acid, 1-amino-2-phenyl-cyclopropanecarboxylic acid, 1-amino-cyclobutanecarboxylic acid, 4-amino-cyclopentenecarboxylic acid, 3-amino-cyclohexanecarboxylic acid, 4-piperidylacetic acid, 4-amino-1-methylpyrrole-2-carboxylic acid, 2,4-diaminobutyric acid, 2,3-diaminopropionic acid, 2,4-diaminobutyric acid, 2-aminoheptanedioic acid, 4-(aminomethyl)benzoic acid, 4-aminobenzoic acid, ortho-, meta- and/para-substituted phenylalanines (e.g., substituted with —C(=O)C$_6$H$_5$; —CF$_3$; —CN; -halo; —NO2; CH$_3$), disubstituted phenylalanines, substituted tyrosines (e.g., further substituted with -Q=O) C$_6$H$_5$; —CF$_3$; —CN; -halo; —NO$_2$; CH$_3$), and statine. Additionally, amino acids can be derivatized to include amino acid residues that are hydroxylated, phosphorylated, sulfonated, acylated, and glycosylated.

Also, one or more of the amino acids in a peptide or peptide may be modified, for example, by the addition of a chemical entity such as a carbohydrate group, a hydroxyl group, a phosphate group, a farnesyl group, an isofarnesyl group, a fatty acid group, a linker for conjugation, functionalization, or other modification, etc. A peptide or peptide may also be a single molecule or may be a multi-molecular complex, such as a protein. A peptide or peptide may be just a fragment of a naturally occurring protein or peptide. A peptide or peptide may be naturally occurring, recombinant, or synthetic, or any combination thereof.

In some instances, peptides can include (e.g., comprise, consist essentially of, or consist of) at least seven (e.g., 7, 8, 9, 10, 11, 12) contiguous amino acids of the sequence of SEQ ID NO: 1 or 2.

Examples of chemical synthesis technologies are solid phase synthesis and liquid phase synthesis. As a solid phase synthesis, for example, the amino acid corresponding to the C-terminus of the peptide to be synthesized is bound to a support which is insoluble in organic solvents, and by alternate repetition of reactions, one wherein amino acids with their amino groups and side chain functional groups protected with appropriate protective groups are condensed one by one in order from the C-terminus to the N-terminus, and one where the amino acids bound to the resin or the protective group of the amino groups of the peptides are released, the peptide chain is thus extended in this manner. Solid phase synthesis methods are largely classified by the tBoc method and the Fmoc method, depending on the type of protective group used. Typically used protective groups include tBoc (t-butoxycarbonyl), Cl—Z (2-chlorobenzyloxycarbonyl), Br—Z (2-bromobenzyloyycarbonyl), Bzl (benzyl), Fmoc (9-fluorenylmethoxycarbonyl), Mbh (4,4'-dimethoxydibenzhydryl), Mtr (4-methoxy-2,3,6-trimethylbenzenesulphonyl), Trt (trityl), Tos (tosyl), Z (benzyloxycarbonyl) and Clz-Bzl (2,6-dichlorobenzyl) for the amino groups; NO2 (nitro) and Pmc (2,2,5,7,8-pentamethylchromane-6-sulphonyl) for the guanidino groups); and tBu (t-butyl) for the hydroxyl groups). After synthesis of the desired peptide, it is subjected to the de-protection reaction and cut out from the solid support. Such peptide cutting reaction may be carried with hydrogen fluoride or trifluoromethane sulfonic acid for the Boc method, and with TFA for the Fmoc method.

Alternatively, the peptide may be synthesized using recombinant techniques. The CDK5 peptide inhibitors may be expressed as isolated nucleic acids encoding the peptide. The isolated nucleic acid sequence may comprise RNA or DNA. As used herein, "isolated nucleic acids" are those that have been removed from their normal surrounding nucleic acid sequences in the genome or in cDNA sequences. Such isolated nucleic acid sequences may comprise additional sequences useful for promoting expression and/or purification of the encoded peptide, including but not limited to polyA sequences, modified Kozak sequences, and sequences encoding epitope tags, export signals, and secretory signals, nuclear localization signals, and plasma membrane localization signals.

Thus, in another aspect, the present invention provides recombinant expression vectors comprising the isolated nucleic acid of any aspect of the invention operatively linked to a suitable control sequence. "Recombinant expression vector" includes vectors that operatively link a nucleic acid coding region or gene to any control sequences capable of effecting expression of the gene product. "Control sequences" operably linked to the nucleic acid sequences of the invention are nucleic acid sequences capable of effecting the expression of the nucleic acid molecules. The control sequences need not be contiguous with the nucleic acid sequences, so long as they function to direct the expression thereof. Thus, for example, intervening untranslated yet transcribed sequences can be present between a promoter sequence and the nucleic acid sequences and the promoter sequence can still be considered "operably linked" to the coding sequence. Other such control sequences include, but are not limited to, polyadenylation signals, termination signals, and ribosome binding sites. Such expression vectors can be of any type known in the art, including but not limited plasmid and viral-based expression vectors. The control sequence used to drive expression of the disclosed nucleic acid sequences in a mammalian system may be constitutive (driven by any of a variety of promoters, including but not limited to, CMV, SV40, RSV, actin, EF) or inducible (driven by any of a number of inducible promoters including, but not limited to, tetracycline, ecdysone, steroid-responsive). The construction of expression vectors for use in transfecting host cells is well known in the art, and thus can be accomplished via standard techniques.

The method of producing the peptide may optionally comprise the steps of purifying said peptide, and/or chemically modifying said peptide.

The methods of the invention may be used to promote cognitive function in a normal subject or to treat a subject having a cognitive dysfunction. A normal subject, as used herein, is a subject that has not been diagnosed with a disorder associated with impaired cognitive function.

"Cognitive function" refers to mental processes of an animal or human subject relating to information gathering and/or processing; the understanding, reasoning, and/or application of information and/or ideas; the abstraction or specification of ideas and/or information; acts of creativity, problem-solving, and possibly intuition; and mental processes such as learning, perception, and/or awareness of ideas and/or information. The mental processes are distinct from those of beliefs, desires, and the like. In some embodiments, cognitive function may be assessed, and thus optionally defined, via one or more tests or assays for cognitive function. Non-limiting examples of a test or assay for cognitive function include CANTAB (see for example Fray et al. "CANTAB battery: proposed utility in neurotoxicology."*Neurotoxicol Teratol.* 1996; 18 (4):499-504), Stroop Test, Trail Making, Wechsler Digit Span, or the CogState computerized cognitive test (see also Dehaene et al. "Reward-dependent learning in neuronal networks for planning and decision making. *Brain Res.* 2000; 126:21729; Iverson et al. "Interpreting change on the WAIS-III/WMS-III in clinical samples." *Arch Clin Neuropsychol.* 2001; 16 (2):183-91; and Weaver et al. "Mild memory impairment in healthy older adults is distinct from normal aging." Cogn. 2006; 60 (2):146-55).

Impaired cognitive function refers to cognitive function that is not as robust as that observed in an age-matched normal subject and includes states in which cognitive function is reduced. In some cases, cognitive function is reduced by about 5%, about 10%, about 30%, or more, compared to cognitive function measured in an age-matched normal subject. Cognitive function may be promoted to any detectable degree, but in humans preferably is promoted sufficiently to allow an impaired subject to carry out daily activities of normal life.

In some embodiments, methods for treating cognitive function disorders or impairments are provided. The methods comprise administering to a subject in need thereof an effective amount of a CDK5i peptide. The CDK5 peptide inhibitor may be administered at a dosage effectively low to maintain an effective cumulative CDK5 peptide inhibitor serum concentration in the subject. The CDK5 peptide inhibitor may be administered once every other day. The CDK5 peptide inhibitor may be administered once, twice, three, four, or five times a day, and/or every other day, every third day, every fourth day, every fifth day, every sixth day, every seventh day, etc. The CDK5 peptide inhibitor may also be administered for at least 1, 2, 3, 4, 5, 6, 7, 8, 9, 10, 11, 12, 13, 14, 15, 16, 17, 18, 19, or 20 days.

In some embodiments, the cognitive function disorders or impairments are associated with, but not limited to, Alzheimer's disease, Huntington's disease, frontotemporal dementia, seizure-induced memory loss, schizophrenia, Rubinstein Taybi syndrome, Rett Syndrome, Fragile X, Lewey body dementia, Vascular dementia, bipolar disorder and social, cognitive and learning disorders associated with autism, ADHD, dyslexia, learning disorders, traumatic head injury, stroke induced cognitive and motor impairment, traumatic brain injury, neurodegeneration and neuronal loss mediated cognitive impairment, and attention deficit disorder. In some embodiments, the cognitive function disorders or impairments are associated with, but not limited to, anxiety disorders, conditioned fear response, panic disorders, obsessive compulsive disorders, post-traumatic stress disorder, phobias, social anxiety disorders, substance dependence recovery or Age Associated Memory Impairment (AAMI), and Age Related Cognitive Decline (ARCD). A person of skill in the art will that the methods of the inventions may be used to treat any condition associated with cognitive function disorders or impairments.

Alzheimer's disease is a degenerative brain disorder characterized by cognitive and noncognitive neuropsychiatric symptoms, which accounts for approximately 60% of all cases of dementia for patients over 65 years old. In Alzheimer's disease, the cognitive systems that control memory have been damaged. Often long-term memory is retained while short-term memory is lost; conversely, memories may become confused, resulting in mistakes in recognizing people or places that should be familiar. Psychiatric symptoms are common in Alzheimer's disease, with psychosis (hallucinations and delusions) present in many patients. It is possible that the psychotic symptoms of Alzheimer's disease involve a shift in the concentration of dopamine or acetylcholine, which may augment a dopaminergic/cholinergic balance, thereby resulting in psychotic behavior. For example, it has been proposed that an increased dopamine release may be responsible for the positive symptoms of schizophrenia. This may result in a positive disruption of the dopaminergic/cholinergic balance. In Alzheimer's disease, the reduction in cholinergic neurons effectively reduces acetylcholine release resulting in a negative disruption of the dopaminergic/cholinergic balance. Indeed, antipsychotic agents that are used to relieve psychosis of schizophrenia are also useful in alleviating psychosis in Alzheimer's patients and could be combined with the compositions described herein for use in the methods of the invention.

Methods for recapturing a memory in a subject having Alzheimer's disease by administering a CDK5 peptide inhibitor or the other related compounds of the invention are also provided according to the invention. Such methods optionally involve administering the inhibitor and monitoring the subject to identify recapture of a memory that was previously lost. Subjects may be monitored by routine tests known in the art. For instance some are described in books such as DSM described above or in the medical literature.

The present invention also provides methods for treating Huntington's disease by administering an effective amount of a CDK5i peptide. Huntington's disease is a neurological disease which results in cognitive decline associated with inexorable progression to death. Cognitive symptoms associated with Huntington's disease include loss of intellectual speed, attention and short term memory and/or behavioral symptoms. In some embodiments, the method of treatment is not selected based on expression levels of Huntington disease biomarker genes selected from the group consisting of ANXA1, AXOT, CAPZA1, HIF1A, JJAZ1, P2Y5, PCNP, ROCK1 (p160ROCK), SF3B1, SP3, TAF7 and YIPPEE. In some embodiments, the diagnosis and the method of treatment are not selected based on expression levels of Huntington disease biomarker genes disclosed in US patent application US 2007/0015183. In some embodiments, the diagnosis and the method of treatment are selected based on medical history, family history or brain imaging tests.

The present invention further provides methods for treating frontotemporal dementia (FTD) by administering an effective amount of a CDK5i peptide. FTD is a neurological disease which results in cognitive decline associated with progressive neuronal loss, typically in the frontal and temporal lobes of the brain. Cognitive symptoms associated with FTD include changes in social and personal behavior, apathy, blunting of emotions, and deficits in both expressive and receptive language. The diagnosis and the method of treatment may be selected based on medical history, family, history, neuropsychological tests, or brain imaging tests.

As used herein, treating condition or patient refers to taking steps to obtain beneficial or desired results, including clinical results. Beneficial or desired clinical results include, but are not limited to, alleviation or amelioration of one or more symptoms associated with disorders involving cognitive dysfunction, diminishment of extent of disease, delay or slowing of disease progression, amelioration, palliation or stabilization of the disease state, and other beneficial results, such as improvement of cognitive function or a reduced rate of decline of cognitive function.

In some embodiments, the subject may undergo additional therapies to treat the disorder in addition to the CDK5i peptide. The combination therapies may be any type of therapy appropriate for treating the particular disease. For instance the combination therapy may be behavioral therapy or medicaments. Behavioral therapy comprises, but is not limited to, electroconvulsive seizure therapy, exercise, group therapy, talk therapy, or conditioning. In another embodiment, the behavioral therapy is cognitive-behavioral therapy. Examples of behavioral therapy that may be used in the ongoing methods are described, for example, in Cognitive-Behavioral Therapies by K. Dobson, ed., Guilford Publications, Inc., 2002; The New Handbook of Cognitive Therapy Techniques by Rian E. McMullin; Norton, W. W. & Company, Inc., 2000; and Cognitive Therapy: Basics and Beyond by Judith S. S. Beck, Guilford Publications, Inc., 1995, herein incorporated by reference in their entireties.

The CDK5 peptide inhibitor may be administered on a recurring basis, such as daily, weekly, or monthly in one or more doses. It may be administered preventatively; i.e., before symptoms appear on a regular basis (daily, weekly, monthly, etc.), and in some cases, it may be administered on a non-regular basis e.g. whenever symptoms begin.

The CDK5 peptide inhibitor may be administered orally, transdermally, intravenously, cutaneously, subcutaneously, nasally, intramuscularly, intraperitoneally, intracranially, or intracerebroventricularly.

The invention also relates to improving cognitive function in a normal subject by administering an effective amount of CDK5 peptide inhibitor. Improving cognitive function includes promoting cognitive function in the subject so that it more closely resembles or exceeds the function of an age-matched normal, unimpaired subject. A normal subject is a subject that has not been diagnosed with any disorder or condition associated with impaired cognitive function. Cognitive performance of a subject is influenced by a variety of factors and the methods of the invention can be practiced to counteract any factors, for example, sleep deprivation, mental exhaustion, physical exhaustion or overexertion.

A subject shall mean a human or vertebrate animal or mammal including but not limited to a dog, cat, horse, cow, pig, sheep, goat, turkey, chicken, and primate, e.g., monkey. In some embodiments subjects are those which are not otherwise in need of CDK5 and/or p25 inhibitor. Human subjects are preferred.

The term effective amount of the therapeutic compounds of the invention refers to the amount necessary or sufficient to realize a desired biologic effect. For example, an effective amount of a therapeutic compounds of the invention is that amount sufficient to re-establish access to a memory. Combined with the teachings provided herein, by choosing among the various active compounds and weighing factors such as potency, relative bioavailability, patient body weight, severity of adverse side-effects and preferred mode of administration, an effective prophylactic or therapeutic treatment regimen can be planned which does not cause substantial toxicity and yet is entirely effective to treat the particular subject. The effective amount for any particular application can vary depending on such factors as the disease or condition being treated, the particular therapeutic compounds being administered the size of the subject, or the severity of the disease or condition. One of ordinary skill in the art can empirically determine the effective amount of a particular therapeutic compounds of the invention without necessitating undue experimentation.

In one example, the effective amount of a CDK5 peptide inhibitor of the present disclosure can vary from about 100 μg-100 mg per kg body weight if administered intravenously. In some embodiments, a therapeutically effective amount is between 10 to 100 mg/kg body weight administered intraperitoneally, including 20 to 80 mg/kg body weight, 30 to 70 mg/kg body weight, or 40 to 60 mg/kg, such as about 20 mg/kg, about 30 mg/kg, about 40 mg/kg, about 45 mg/kg, about 50 mg/kg, about 55 mg/kg, about 60 mg/kg, 70 mg/kg, about 80 mg/kg or about 90 mg/kg. The doses may be given singularly or in divided doses. The amount of the CDK5 peptide inhibitor to be administered is determined in light of various relevant factors, such as the condition to be treated, the selected route of administration, the age, sex, and weight of the subject, and the severity of the subject's symptoms, among other factors, all of which are known to one of ordinary skill in the art. The exemplary doses should not limit the scope of the invention in any way.

Subject doses of the compounds described herein for delivery typically may be administered once a day for a series of consecutive days, which depending on the application could be given daily, weekly, or monthly and any other amount of time there between. In one embodiment, the composition is administered once a day for at least 2 consecutive days. In another embodiment, the therapeutic compounds (CDK5 peptide inhibitor and pharmaceutically acceptable carrier) are administered once every other day, or once a day with at least 2 days between doses. Since there is some variance in humans at a given dose the dose may be personalized in some instances. Such manipulation is within the skill of the ordinary artisan in view of the teachings found herein.

The desired biologic effect may be the reduction or inhibition of one or more symptoms associated with the neurodegenerative disease. The one or more symptoms do not have to be fully (i.e., 100%) eliminated in order to have a desired biologic effect. For example, administration of a CDK5 peptide inhibitor may reduce the symptom(s) by a desired amount, such as at least 20%, at least 30%, at least 40%, at least 50%, at least 60%, at least 70%, at least 80%, at least 90%, at least 91%, at least 92%, at least 93%, at least 94%, at least 95%, at least 96%, at least 97%, at least 98%, at least 99%, or at least 100% (i.e., fully) as compared to the symptom without treatment. Alternatively, the desired biologic effect may be the reduction or inhibition of CDK5 kinase activity in the brain.

The formulations of the invention are administered in pharmaceutically acceptable solutions, which may routinely contain pharmaceutically acceptable concentrations of salt, buffering agents, preservatives, compatible carriers, and optionally other therapeutic ingredients.

For use in therapy, an effective amount of the therapeutic compounds of the invention can be administered to a subject by any mode that delivers the therapeutic agent or compound to the desired surface, e.g., mucosal, systemic. Administering the pharmaceutical composition of the present invention may be accomplished by any means known to the skilled artisan. The invention provides pharmaceutical composition, comprising a peptide of any embodiment or combination of embodiments of the invention, and a pharmaceutically acceptable carrier. The pharmaceutical composition may comprise in addition to the peptide of the invention (a) a lyoprotectant; (b) a surfactant; (c) a bulking agent; (d) a tonicity adjusting agent; (e) a stabilizer; (f) a preservative and/or (g) a buffer. A lyoprotectant, may include, for instance, sucrose, sorbitol or trehalose. In other embodiments, the pharmaceutical composition additionally includes a stabilizer, e.g., a molecule which, when combined with a peptide substantially prevents or reduces chemical and/or physical instability of the peptide in lyophilized or liquid form. Exemplary stabilizers include sucrose, sorbitol, glycine, inositol, sodium chloride, methionine, arginine, and arginine hydrochloride.

For oral administration, the therapeutic compounds of the invention can be formulated readily by combining the active compound(s) with pharmaceutically acceptable carriers well known in the art. Such carriers enable the compounds of the invention to be formulated as tablets, pills, dragees, capsules, liquids, gels, syrups, slurries, suspensions and the like, for oral ingestion by a subject to be treated. Pharmaceutical preparations for oral use can be obtained as solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Optionally the oral formulations may also be formulated in saline or buffers, i.e. EDTA for neutralizing internal acid conditions or may be administered without any carriers.

Also specifically contemplated are oral dosage forms of the above component or components. The component or components may be chemically modified so that oral delivery of the derivative is efficacious. Generally, the chemical modification contemplated is the attachment of at least one moiety to the component molecule itself, where said moiety permits (a) inhibition of proteolysis; and (b) uptake into the blood stream from the stomach or intestine. Also desired is the increase in overall stability of the component or components and increase in circulation time in the body. Examples of such moieties include: polyethylene glycol, copolymers of ethylene glycol and propylene glycol, carboxymethyl cellulose, dextran, polyvinyl alcohol, polyvinyl pyrrolidone and polyproline. Other polymers that could be used are poly-1,3-dioxolane and poly-1,3,6-tioxocane and polyethylene glycol moieties.

In some embodiments, the polymer is a block polymer and comprises a hydrophilic block and an endosomolytic block. Any suitable hydrophilic block and endosomolytic blocks may be used. In one embodiment, the hydrophilic block comprises polyethylene glycol methacrylate. In another embodiment, the endosomolytic block comprises a diethylaminoethyl methacrylate-butyl methacrylate copolymer. In a further embodiment, the polymer is a stimuli-responsive polymer that responds to one or more stimuli selected from the group consisting of pH, temperature, UV-visible light, photo-irradiation, exposure to an electric field, ionic strength, and the concentration of certain chemicals by exhibiting a property change. As used herein, a "stimuli-responsive polymer" is a polymer that changes its associative properties in response to a stimulus. The stimuli-responsive polymer responds to changes in external stimuli such as the pH, temperature, UV-visible light, photo-irradiation, exposure to an electric field, ionic strength, and the concentration of certain chemicals by exhibiting property change. The chemicals could be polyvalent ions such as calcium ion, polyions of either charge, or enzyme substrates such as glucose. For example, a temperature-responsive polymer may be responsive to changes in temperature by exhibiting a lower critical solution temperature in aqueous solution. A stimuli-responsive polymer may be a multi-responsive polymer, where the polymer exhibits property change in response to combined simultaneous or sequential changes in two or more external stimuli. The stimuli-responsive polymers may be synthetic or natural polymers that exhibit reversible conformational or physico-chemical changes such as folding/unfolding transitions, reversible precipitation behavior, or other conformational changes to in response to stimuli, such as to changes in temperature, light, pH, ions, or pressure. Representative stimuli-responsive polymers include temperature-sensitive polymers, pH-sensitive polymers, and light-sensitive polymers.

The location of release may be the stomach, the small intestine (the duodenum, the jejunum, or the ileum), or the large intestine. One skilled in the art has available formulations which will not dissolve in the stomach, yet will release the material in the duodenum or elsewhere in the intestine. Preferably, the release will avoid the deleterious effects of the stomach environment, either by protection of the therapeutic agent or by release of the biologically active material beyond the stomach environment, such as in the intestine.

To ensure full gastric resistance a coating impermeable to at least pH 5.0 is important. Examples of the more common inert ingredients that are used as enteric coatings are cellulose acetate trimellitate (CAT), hydroxypropylmethylcellulose phthalate (HPMCP), HPMCP 50, HPMCP 55, polyvinyl acetate phthalate (PVAP), Eudragit L30D, Aquateric, cellulose acetate phthalate (CAP), Eudragit L, Eudragit S, and Shellac. These coatings may be used as mixed films.

A coating or mixture of coatings can also be used on tablets, which are not intended for protection against the stomach. This can include sugar coatings, or coatings which make the tablet easier to swallow. Capsules may consist of a hard shell (such as gelatin) for delivery of dry therapeutic i.e. powder; for liquid forms, a soft gelatin shell may be used. The shell material of cachets could be thick starch or other edible paper. For pills, lozenges, molded tablets or tablet triturates, moist massing techniques can be used.

The therapeutic can be included in the formulation as line multi-particulates in the form of granules or pellets of particle size about 1 mm. The formulation of the material for capsule administration could also be as a powder, lightly compressed plugs or even as tablets. The therapeutic could be prepared by compression.

Colorants and flavoring agents may all be included. For example, the therapeutic agent may be formulated (such as by liposome or microsphere encapsulation) and then further contained within an edible product, such as a refrigerated beverage containing colorants and flavoring agents.

One may dilute or increase the volume of the therapeutic with an inert material. These diluents could include carbohydrates, especially mannitol, a-lactose, anhydrous lactose, cellulose, sucrose, modified dextrans and starch. Certain inorganic salts may be also be used as fillers including calcium triphosphate, magnesium carbonate and sodium chloride. Some commercially available diluents are Fast-Flo, Emdex, STA-Rx 1500, Emcompress and Avicell.

Disintegrants may be included in the formulation of the therapeutic into a solid dosage form. Materials used as disintegrates include but are not limited to starch, including the commercial disintegrant based on starch, Explotab. Sodium starch glycolate, Amberlite, sodium carboxymethylcellulose, ultramylopectin, sodium alginate, gelatin, orange peel, acid carboxymethyl cellulose, natural sponge and bentonite may all be used. Another form of the disintegrants are the insoluble cationic exchange resins. Powdered gums may be used as disintegrants and as binders and these can include powdered gums such as agar, Karaya or tragacanth. Alginic acid and its sodium salt are also useful as disintegrants. Binders may be used to hold the therapeutic agent together to form a hard tablet and include materials from natural products such as acacia, tragacanth, starch and gelatin. Others include methyl cellulose (MC), ethyl cellulose (EC) and carboxymethyl cellulose (CMC). Polyvinyl pyrrolidone (PVP) and hydroxypropylmethyl cellulose (HPMC) could both be used in alcoholic solutions to granulate the therapeutic.

An anti-frictional agent may be included in the formulation of the therapeutic to prevent sticking during the formulation process. Lubricants may be used as a layer between the therapeutic and the die wall, and these can include but are not limited to stearic acid including its magnesium and calcium salts, polytetrafluoroethylene (PTFE), liquid paraffin, vegetable oils and waxes. Soluble lubricants may also be used such as sodium lauryl sulfate, magnesium lauryl sulfate, polyethylene glycol of various molecular weights, Carbowax 4000 and 6000.

Glidants that might improve the flow properties of the drug during formulation and to aid rearrangement during compression might be added. The glidants may include starch, talc, pyrogenic silica and hydrated silicoaluminate.

To aid dissolution of the therapeutic into the aqueous environment a surfactant might be added as a wetting agent. Surfactants may include anionic detergents such as sodium lauryl sulfate, dioctyl sodium sulfosuccinate and dioctyl sodium sulfonate. Cationic detergents might be used and could include benzalkonium chloride or benzethomium chloride. The list of potential non-ionic detergents that could be included in the formulation as surfactants are lauromacrogol 400, polyoxyl 40 stearate, polyoxyethylene hydrogenated castor oil 10, 50 and 60, glycerol monostearate, polysorbate 40, 60, 65 and 80, sucrose fatty acid ester, methyl cellulose and carboxyl methyl cellulose. These surfactants could be present in the formulation of the therapeutic agent either alone or as a mixture in different ratios.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Microspheres formulated for oral administration may also be used. Such microspheres have been well defined in the art. All formulations for oral administration should be in dosages suitable for such administration.

For buccal administration, the compositions may take the form of tablets or lozenges formulated in conventional manner.

For administration by inhalation, the compounds for use according to the present invention may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

Contemplated for use in the practice of this invention are a wide range of mechanical devices designed for pulmonary delivery of therapeutic products, including but not limited to nebulizers, metered dose inhalers, and powder inhalers, all of which are familiar to those skilled in the art.

Some specific examples of commercially available devices suitable for the practice of this invention are the Ultravent nebulizer, manufactured by Mallinckrodt, Inc., St. Louis, Missouri; the Acorn II nebulizer, manufactured by Marquest Medical Products, Englewood, Colorado; the Ventolin metered dose inhaler, manufactured by Glaxo Inc., Research Triangle Park, North Carolina; and the Spinhaler powder inhaler, manufactured by Fisons Corp., Bedford, Massachusetts.

All such devices require the use of formulations suitable for the dispensing of therapeutic agent. Typically, each formulation is specific to the type of device employed and may involve the use of an appropriate propellant material, in addition to the usual diluents, and/or carriers useful in therapy. Also, the use of liposomes, microcapsules or microspheres, inclusion complexes, or other types of carriers is contemplated. Chemically modified therapeutic agent may also be prepared in different formulations depending on the type of chemical modification or the type of device employed.

Formulations suitable for use with a nebulizer, either jet or ultrasonic, will typically comprise therapeutic agent dissolved in water. The formulation may also include a buffer and a simple sugar (e.g., for stabilization and regulation of osmotic pressure). The nebulizer formulation may also contain a surfactant, to reduce or prevent surface induced aggregation of the compound caused by atomization of the solution in forming the aerosol. Formulations for use with a metered-dose inhaler device will generally comprise a finely divided powder containing the therapeutic agent suspended in a propellant with the aid of a surfactant. The propellant may be any conventional material employed for this purpose, such as a chlorofluorocarbon, a hydrochlorofluorocarbon, a hydrofluorocarbon, or a hydrocarbon, including trichlorofluoromethane, dichlorodifluoromethane, dichlorotetrafluoroethanol, and 1,1,2-tetrafluoroethane, or combinations thereof. Suitable surfactants include sorbitan trioleate and soya lecithin. Oleic acid may also be useful as a surfactant.

Formulations for dispensing from a powder inhaler device will comprise a finely divided dry powder containing therapeutic agent and may also include a bulking agent, such as lactose, sorbitol, sucrose, or mannitol in amounts which facilitate dispersal of the powder from the device, e.g., 50 to 90% by weight of the formulation. The therapeutic agent should most advantageously be prepared in particulate form with an average particle size of less than 10 mm (or microns), most preferably 0.5 to 5 mm, for most effective delivery to the distal lung.

Nasal delivery of a pharmaceutical composition of the present invention is also contemplated. Nasal delivery allows the passage of a pharmaceutical composition of the present invention to the blood stream directly after administering the therapeutic product to the nose, without the necessity for deposition of the product in the lung. Formulations for nasal delivery include those with dextran or cyclodextran.

For nasal administration, a useful device is a small, hard bottle to which a metered dose sprayer is attached. In one embodiment, the metered dose is delivered by drawing the pharmaceutical composition of the present invention solution into a chamber of defined volume, which chamber has an aperture dimensioned to aerosolize and aerosol formulation by forming a spray when a liquid in the chamber is compressed. The chamber is compressed to administer the pharmaceutical composition of the present invention. In a specific embodiment, the chamber is a piston arrangement. Such devices are commercially available.

Alternatively, a plastic squeeze bottle with an aperture or opening dimensioned to aerosolize an aerosol formulation by forming a spray when squeezed is used. The opening is usually found in the top of the bottle, and the top is generally tapered to partially fit in the nasal passages for efficient administration of the aerosol formulation. Preferably, the nasal inhaler will provide a metered amount of the aerosol formulation, for administration of a measured dose of the drug.

The compounds, when it is desirable to deliver them systemically, may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active compounds may be in powder form for constitution with a suitable vehicle, e.g., sterile pyrogen-free water, before use.

In addition to the formulations described previously, the compounds may also be formulated as a depot preparation. Such long acting formulations may be formulated with suitable polymeric or hydrophobic materials for example as an emulsion in an acceptable oil) or ion exchange resins, or as sparingly soluble derivatives, for example, as a sparingly soluble salt.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Suitable liquid or solid pharmaceutical preparation forms are, for example, aqueous or saline solutions for inhalation, microencapsulated, encochleated, coated onto microscopic gold particles, contained in liposomes, nebulized, aerosols, pellets for implantation into the skin, or dried onto a sharp object to be scratched into the skin. The pharmaceutical compositions also include granules, powders, tablets, coated tablets, (micro)capsules, suppositories, syrups, emulsions, suspensions, creams, drops or preparations with protracted release of active compounds, in whose preparation excipients and additives and/or auxiliaries such as disintegrants, binders, coating agents, swelling agents, lubricants, flavorings, sweeteners or solubilizers are customarily used as described above. The pharmaceutical compositions are suitable for use in a variety of drug delivery systems. For a brief review of methods for drug delivery, see Langer, *Science* 249:1527-1533, 1990, which is incorporated herein by reference.

The therapeutic compounds of the invention and optionally other therapeutics may be administered per se (neat) or in the form of a pharmaceutically acceptable salt. When used in medicine the salts should be pharmaceutically acceptable, but non-pharmaceutically acceptable salts may conveniently be used to prepare pharmaceutically acceptable salts thereof. Such salts include, but are not limited to, those prepared from the following acids: hydrochloric, hydrobromic, sulphuric, nitric, phosphoric, maleic, acetic, salicylic, p-toluene sulphonic, tartaric, citric, methane sulphonic, formic, malonic, succinic, naphthalene-2-sulphonic, and benzene sulphonic. Also, such salts can be prepared as alkaline metal or alkaline earth salts, such as sodium, potassium or calcium salts of the carboxylic acid group.

Suitable buffering agents include: acetic acid and a salt (e.g., 1-2% w/v); citric acid and a salt (e.g., 1-3% w/v); boric acid and a salt (e.g., 0.5-2.5% w/v); and phosphoric acid and a salt (e.g., 0.8-2% w/v). Suitable preservatives include benzalkonium chloride (e.g., 0.003-0.03% w/v); chlorobutanol (e.g., 0.3-0.9% v/v); parabens (e.g., 0.01-0.25% w/v) and thimerosal 0.004-0.02% w/v).

The pharmaceutical compositions of the invention contain an effective amount of a therapeutic compound of the invention optionally included in a pharmaceutically-acceptable carrier. The term pharmaceutically-acceptable carrier means one or more compatible solid or liquid filler, diluents or encapsulating substances which are suitable for administration to a human or other vertebrate animal. The term carrier denotes an organic or inorganic ingredient, natural or synthetic, with which the active ingredient is combined to facilitate the application. The components of the pharmaceutical compositions also are capable of being commingled with the compounds of the present invention, and with each other, in a manner such that there is no interaction which would substantially impair the desired pharmaceutical efficiency.

The therapeutic agents may be delivered to the brain using a formulation capable of delivering a therapeutic agent across the blood brain barrier. One obstacle to delivering therapeutics to the brain is the physiology and structure of the brain. The blood-brain barrier is made up of specialized capillaries lined with a single layer of endothelial cells. The region between cells are sealed with a tight junction, so the only access to the brain from the blood is through the endothelial cells. The barrier allows only certain substances, such as lipophilic molecules through and keeps other harmful compounds and pathogens out. Thus, lipophilic carriers are useful for delivering non-lipophilic compounds to the brain. For instance, DHA, a fatty acid naturally occurring in the human brain has been found to be useful for delivering drugs covalently attached thereto to the brain (Such as those described in U.S. Pat. No. 6,407,137). U.S. Pat. No. 5,525,727 describes a dihydropyridine pyridinium salt carrier redox system for the specific and sustained delivery of drug species to the brain. U.S. Pat. No. 5,618,803 describes targeted drug delivery with phosphonate derivatives. U.S. Pat. No. 7,119,074 describes amphiphilic prodrugs of a therapeutic compound conjugated to an PEG-oligomer/polymer for delivering the compound across the blood brain barrier. The compounds described herein may be modified by covalent attachment to a lipophilic carrier or co-formulation with a lipophilic carrier. Others are known to those of skill in the art.

The therapeutic agents of the invention may be delivered with other therapeutics for enhancing memory retrieval or treating other symptoms or causes of disorders associated with the memory loss. For instance, environmental enrichment (EE) has been used for enhancing memories. EE involves creating a stimulating environment around a subject. Other therapeutics may also be combined to treat the underlying disorder or to enhance memory recall.

Examples of combinations of the compounds of the present invention with other drugs in either unit dose or kit form include combinations with: anti-Alzheimer's agents, beta-secretase inhibitors, gamma-secretase inhibitors, HMG-CoA reductase inhibitors, NSAIDs including ibuprofen, N-methyl-D-aspartate (NMDA) receptor antagonists, such as memantine, cholinesterase inhibitors such as galantamine, rivastigmine, donepezil, and tacrine, vitamin E, CB-1 receptor antagonists or CB-1 receptor inverse agonists, antibiotics such as doxycycline and rifampin, anti-amyloid antibodies, or other drugs that affect receptors or enzymes that either increase the efficacy, safety, convenience, or reduce unwanted side effects or toxicity of the compounds of the present invention. The foregoing list of combinations is illustrative only and not intended to be limiting in any way.

The invention also includes articles, which refers to any one or collection of components. In some embodiments the articles are kits. The articles include pharmaceutical or diagnostic grade compounds of the invention in one or more containers. The article may include instructions or labels promoting or describing the use of the compounds of the invention.

As used herein, "promoted" includes all methods of doing business including methods of education, hospital and other clinical instruction, pharmaceutical industry activity including pharmaceutical sales, and any advertising or other promotional activity including written, oral and electronic communication of any form, associated with compositions of the invention in connection with treatment of cognitive disorders such as Alzheimer's disease.

"Instructions" can define a component of promotion, and typically involve written instructions on or associated with packaging of compositions of the invention. Instructions also can include any oral or electronic instructions provided in any manner.

Thus the agents described herein may, in some embodiments, be assembled into pharmaceutical or diagnostic or research kits to facilitate their use in therapeutic, diagnostic or research applications. A kit may include one or more containers housing the components of the invention and instructions for use. Specifically, such kits may include one or more agents described herein, along with instructions describing the intended therapeutic application and the proper administration of these agents. In certain embodiments agents in a kit may be in a pharmaceutical formulation and dosage suitable for a particular application and for a method of administration of the agents.

The kit may be designed to facilitate use of the methods described herein by physicians and can take many forms. Each of the compositions of the kit, where applicable, may be provided in liquid form (e.g., in solution), or in solid form, (e.g., a dry powder). In certain cases, some of the compositions may be constitutable or otherwise processable (e.g., to an active form), for example, by the addition of a suitable solvent or other species (for example, water or a cell culture medium), which may or may not be provided with the kit. As used herein, "instructions" can define a component of instruction and/or promotion, and typically involve written instructions on or associated with packaging of the invention. Instructions also can include any oral or electronic instructions provided in any manner such that a user will clearly recognize that the instructions are to be associated with the kit, for example, audiovisual (e.g., videotape, DVD, etc.), Internet, and/or web-based communications, etc. The written instructions may be in a form prescribed by a governmental agency regulating the manufacture, use or sale of pharmaceuticals or biological products, which instructions can also reflects approval by the agency of manufacture, use or sale for human administration.

The kit may contain any one or more of the components described herein in one or more containers. As an example, in one embodiment, the kit may include instructions for mixing one or more components of the kit and/or isolating and mixing a sample and applying to a subject. The kit may include a container housing agents described herein. The agents may be prepared sterilely, packaged in syringe and shipped refrigerated. Alternatively it may be housed in a vial or other container for storage. A second container may have other agents prepared sterilely. Alternatively the kit may include the active agents premixed and shipped in a syringe, vial, tube, or other container.

The kit may have a variety of forms, such as a blister pouch, a shrink wrapped pouch, a vacuum sealable pouch, a sealable thermoformed tray, or a similar pouch or tray form, with the accessories loosely packed within the pouch, one or more tubes, containers, a box or a bag. The kit may be sterilized after the accessories are added, thereby allowing the individual accessories in the container to be otherwise unwrapped. The kits can be sterilized using any appropriate sterilization techniques, such as radiation sterilization, heat sterilization, or other sterilization methods known in the art. The kit may also include other components, depending on the specific application, for example, containers, cell media, salts, buffers, reagents, syringes, needles, a fabric, such as gauze, for applying or removing a disinfecting agent, disposable gloves, a support for the agents prior to administration etc.

The compositions of the kit may be provided as any suitable form, for example, as liquid solutions or as dried powders. When the composition provided is a dry powder, the powder may be reconstituted by the addition of a suitable solvent, which may also be provided. In embodiments where liquid forms of the composition are sued, the liquid form may be concentrated or ready to use. The solvent will depend on the compound and the mode of use or administration. Suitable solvents for drug compositions are well known and are available in the literature. The solvent will depend on the compound and the mode of use or administration.

The kits, in one set of embodiments, may comprise a carrier means being compartmentalized to receive in close confinement one or more container means such as vials, tubes, and the like, each of the container means comprising one of the separate elements to be used in the method. For example, one of the containers may comprise a positive control for an assay. Additionally, the kit may include containers for other components, for example, buffers useful in the assay.

The present invention also encompasses a finished packaged and labeled pharmaceutical product. This article of manufacture includes the appropriate unit dosage form in an appropriate vessel or container such as a glass vial or other container that is hermetically sealed. In the case of dosage forms suitable for parenteral administration the active ingredient is sterile and suitable for administration as a particulate free solution. In other words, the invention encompasses both parenteral solutions and lyophilized powders, each being sterile, and the latter being suitable for reconstitution prior to injection. Alternatively, the unit dosage form may be a solid suitable for oral, transdermal, topical or mucosal delivery.

In another embodiment, compositions of the invention are stored in containers with biocompatible detergents, including but not limited to, lecithin, taurocholic acid, and cholesterol; or with other proteins, including but not limited to, gamma globulins and serum albumins. More preferably, compositions of the invention are stored with human serum albumins for human uses, and stored with bovine serum albumins for veterinary uses.

As with any pharmaceutical product, the packaging material and container are designed to protect the stability of the product during storage and shipment. Further, the products of the invention include instructions for use or other informational material that advise the physician, technician or patient on how to appropriately prevent or treat the disease or disorder in question. In other words, the article of manufacture includes instruction means indicating or suggesting a dosing regimen including, but not limited to, actual doses, monitoring procedures and other monitoring information.

More specifically, the invention provides an article of manufacture comprising packaging material, such as a box, bottle, tube, vial, container, sprayer, insufflator, intravenous (i.v.) bag, envelope and the like; and at least one unit dosage form of a pharmaceutical agent contained within said packaging material. The invention also provides an article of manufacture comprising packaging material, such as a box, bottle, tube, vial, container, sprayer, insufflator, intravenous (i.v.) bag, envelope and the like; and at least one unit dosage form of each pharmaceutical agent contained within said packaging material. The invention further provides an article of manufacture comprising packaging material, such as a box, bottle, tube, vial, container, sprayer, insufflator, intravenous (i.v.) bag, envelope and the like; and at least one unit dosage form of each pharmaceutical agent contained within said packaging material. The invention further provides an article of manufacture comprising a needle or syringe, preferably packaged in sterile form, for injection of the formulation, and/or a packaged alcohol pad.

In a specific embodiment, an article of manufacture comprises packaging material and a pharmaceutical agent and instructions contained within said packaging material, wherein said pharmaceutical agent is a CDK5 peptide inhibitor and a pharmaceutically acceptable carrier, and said instructions indicate a dosing regimen for preventing, treating or managing a subject with cognitive disorders such as Alzheimer's disease.

In some embodiments, the subject may be therapeutically monitored. The adequacy of the treatment parameters chosen, e.g. dose, schedule, and the like, is determined by conventional methods for monitoring memory. In addition, the clinical condition of the patient can be monitored for the desired effect, e.g. increases in cognitive function. If inadequate effect is achieved then the patient can be boosted with further treatment and the treatment parameters can be modified, such as by increasing the amount of the composition of the invention and/or other active agent, or varying the route of administration.

The present invention is further illustrated by the following Examples, which in no way should be construed as further limiting. The entire contents of all of the references (including literature references, issued patents, published patent applications, and co-pending patent applications) cited throughout this application are hereby expressly incorporated by reference.

EXAMPLES

Example 1: Design of CDK5 Inhibitory Peptide

Figure 2:
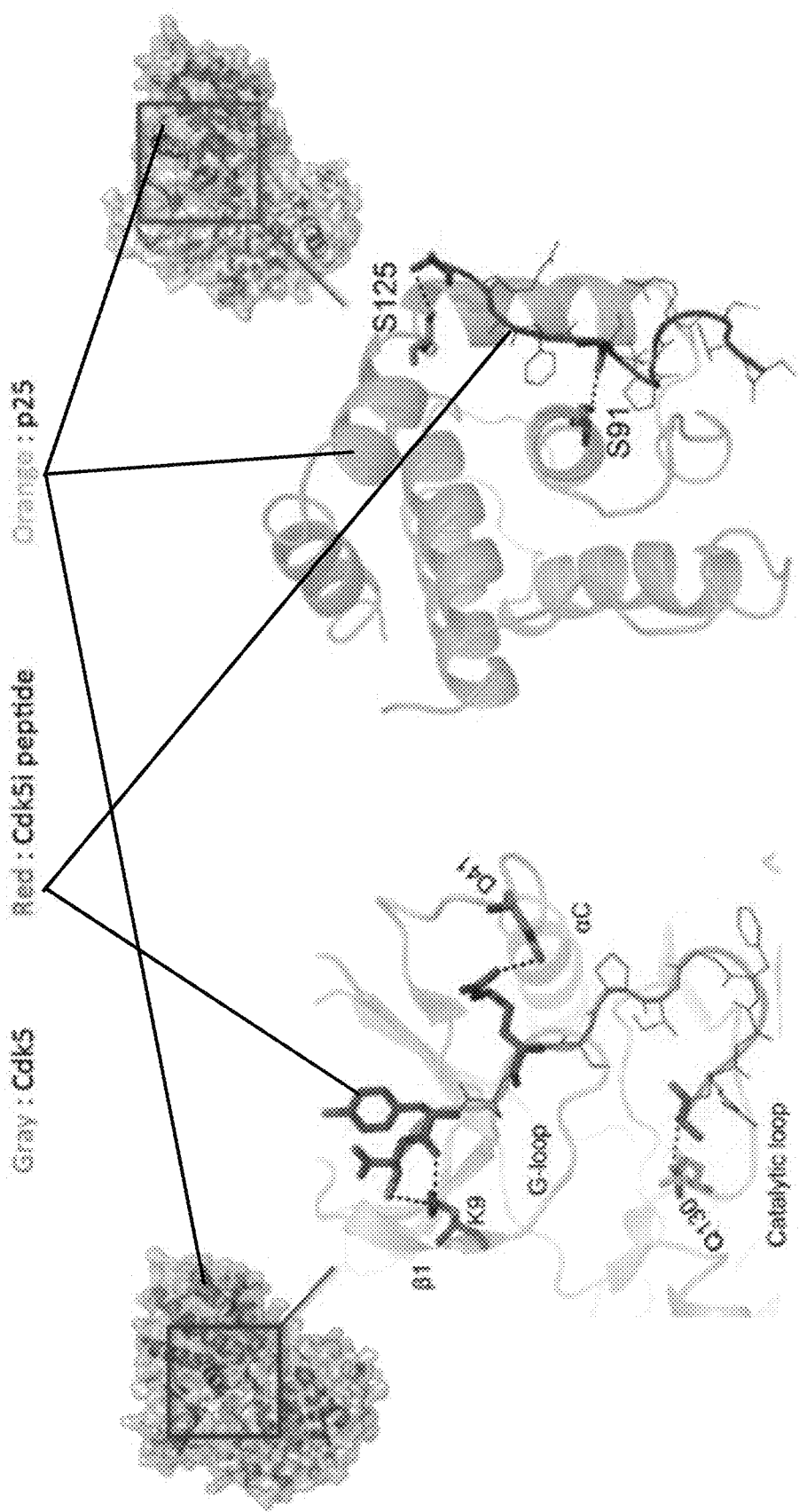
FIG. 2 shows computational modeling, predicting potential interactions of CDK5i peptide with CDK5 (left) and p25 (right).

The region in CDK5 which is essential for its p25 binding has been determined. The sequence of amino acids in the particular region is unique as compared to other CDKs and it is conserved across many species, including human. Therefore, an exemplary 12 amino acid-long peptide (CDK5i, SEQ ID NO: 2) from this region was designed as a potential p25/CDK5 inhibitor (FIGS. 1A-1B). Computation modeling predicted the potential interaction of this CDK5 inhibitory (CDK5i) peptide with both CDK5 and p25. It was also demonstrated that this peptide could interrupt the formation of p25/CDK5 complexes (FIG. 2).

Figure 8:
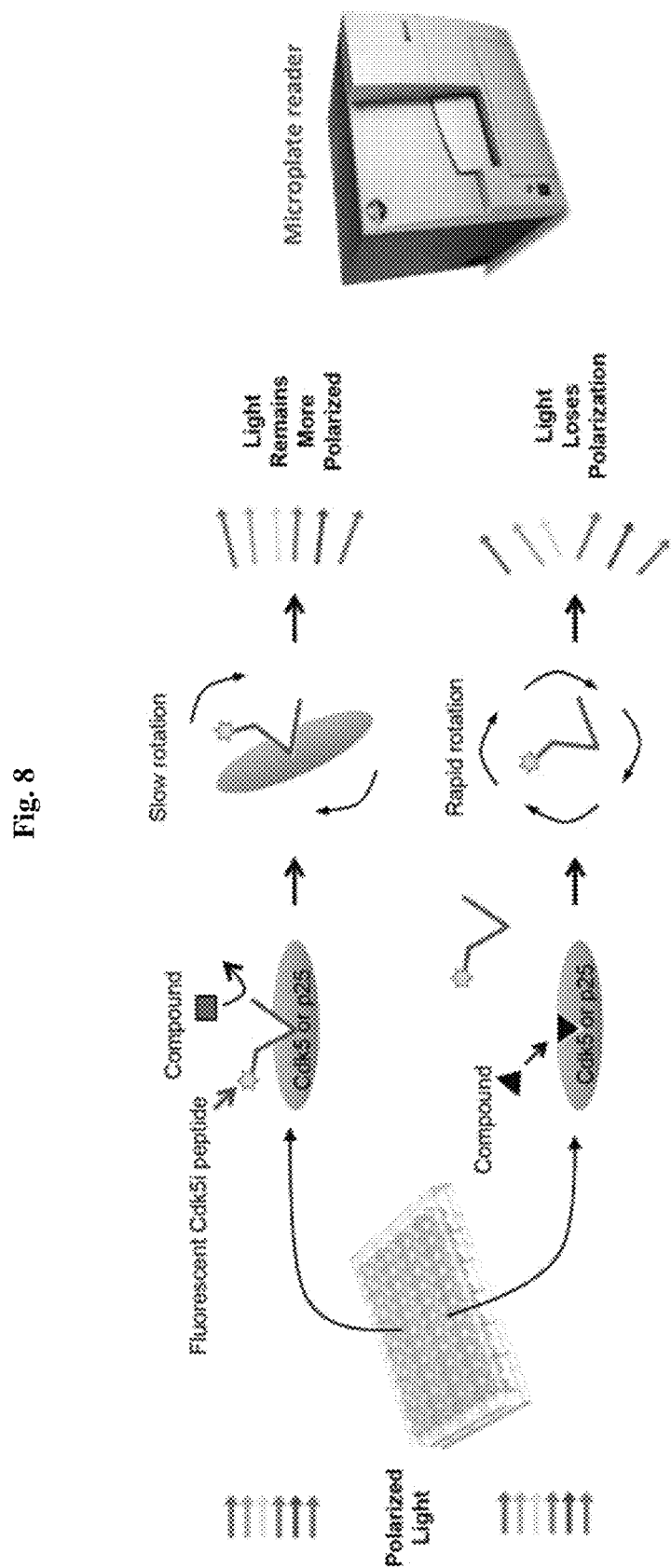
FIG. 8 presents a schematic diagram of fluorescence polarization-high throughput screening used to identify potential CDK5 inhibitory compounds using CDK5i peptide.

The knowledge of the binding site and activity of SEQ ID NO: 2 has led to the design of a set of peptides useful according to the invention. These CDK5 peptide inhibitors can also be used to identify other CDK5 inhibitors using fluorescence-labeled CDK5i (fluorescence polarization-high throughput screen) as shown in FIG. 8.

Example 2: In Vitro Screening of CDK5i Peptide

Figure 3:
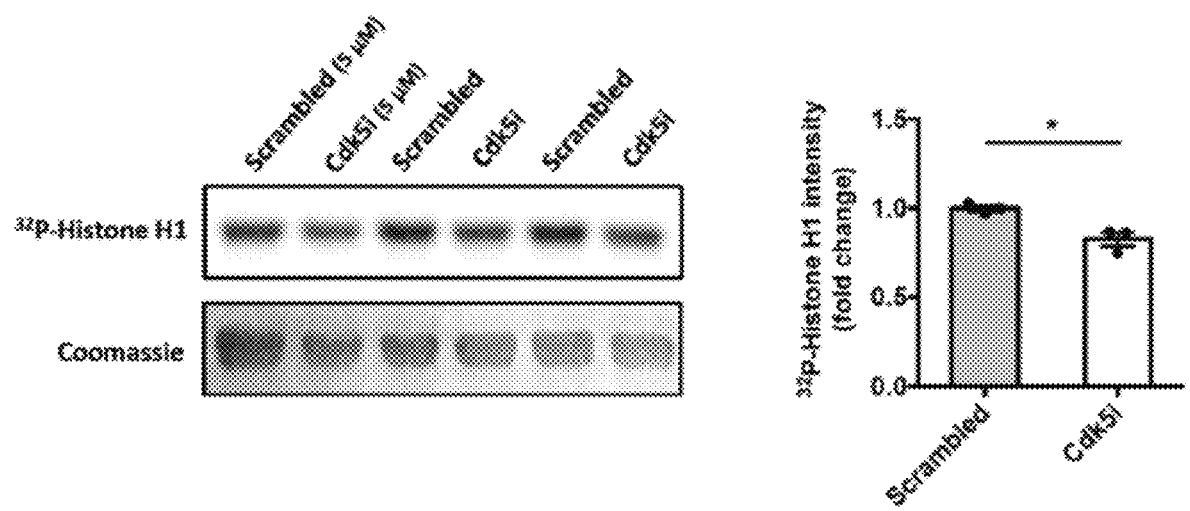
FIG. 3 shows reduced CDK5 activity by CDK5i peptide.

The effect of the peptide (SEQ ID NO: 2) was tested relative to CDK5 activity. Purified recombinant p25/CDK5 complex was incubated with CDK5i peptide and then CDK5 kinase activity was measured using radiolabeled ATP and its substrate, H1. The results show that the CDK5i peptide significantly reduced CDK5 kinase activity compared to that from a scrambled peptide-treated group (FIG. 3).

Figure 4:
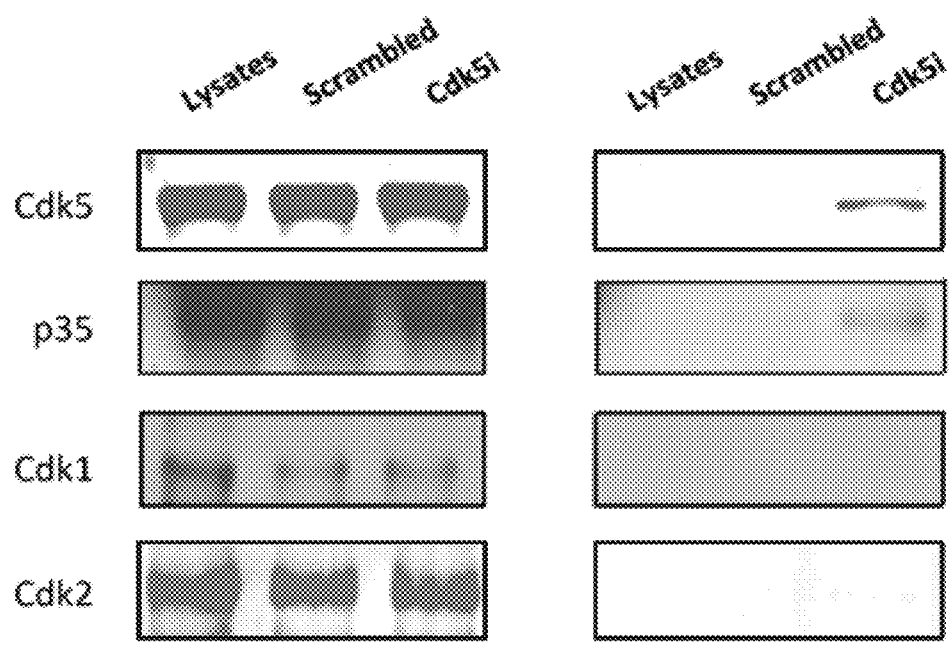
FIG. 4 shows that CDK5i peptide interacts with CDK5 and p35, but not with CDK1 or CDK2.

To determine the effect of the CDK5i peptide in the neurodegenerative brain, brain tissue samples from P301S and control mice were used. P301S mice are used as a model of Alzheimer's disease (AD) and frontotemporal dementia (FTD). As shown in FIG. 4, it was found that the CDK5i peptide physically interacts with CDK5 as well as p35, a precursor of p25, in the brain. However, it does not bind to CDK1 or CDK2, family members highly homologous to CDK5.

The basal activity of CDK5 is indispensable during neurodevelopment. It is also required for various neuronal functions. Unlike pathological conditions, CDK5 activity under physiological conditions is mostly mediated by p24, not p25. To test the effect CDK5i peptide has on basal CDK5 activity, brain tissue from control mice was incubated with CDK5i and no change was found in the basal activity of CDK5 (FIG. 5A). However, CDK5i peptide was shown to significantly reduce the kinase activity of CDK5 in the brain of P301S mice, which usually display hyperactivation of the kinase due to upregulated p25 (FIG. 5B).

Figure 6A:
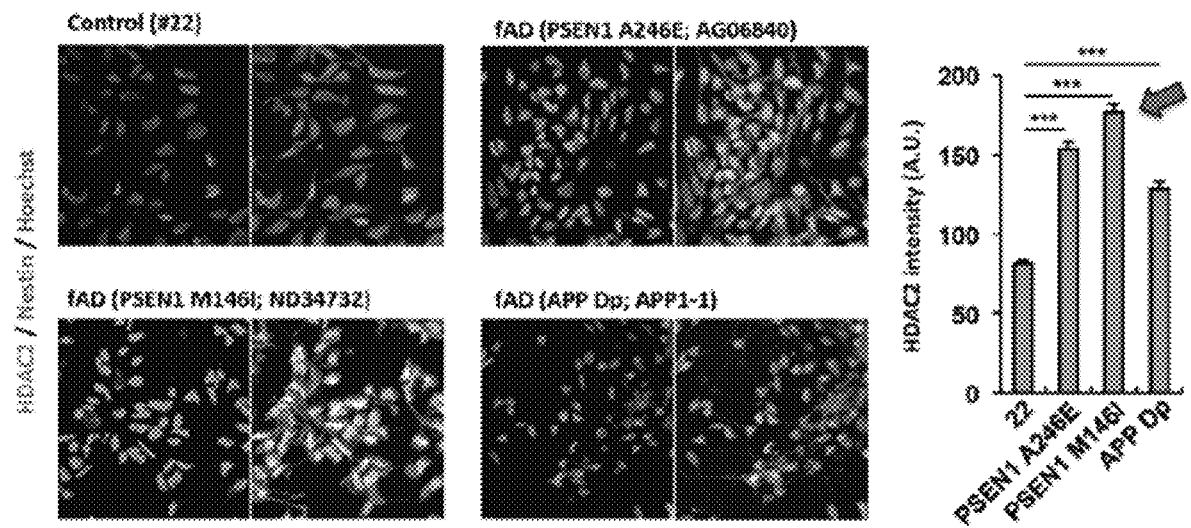
FIGS. 6A-6B show neural progenitor cells (NPCs) from fAD iPSCs demonstrating an upregulation of HDAC2 and increased γH2AX signals, indicative of DNA damage (FIG. 6A), as compared to cells from healthy iPSCs (FIG. 6B).
Figure 6B:
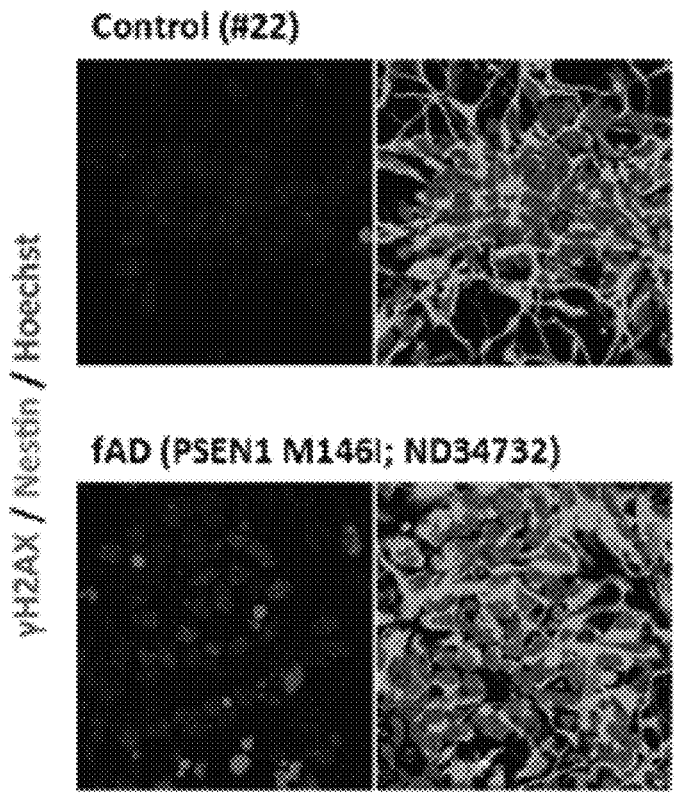

To validate the effect of CDK5i peptide of AD-related pathology in human model systems, induced-pluripotent stem cells (iPSCs) created from fibroblasts of familial AD (fAD) patients were used. Neural progenitor cells (NPCs) derived from fAD iPSCs shows multiple pathological phenotypes, including upregulation of histone deacetylase 2 (HDAC2), which negatively regulates the transcription of genes associated with learning and memory (FIG. 6A). The line carrying the PSEN1 M146I mutation showed the strongest phenotype, and further characterization revealed increase DNA damage in those cells, as compared to NPCs from healthy iPSCs (FIG. 6B).

Figure 7:
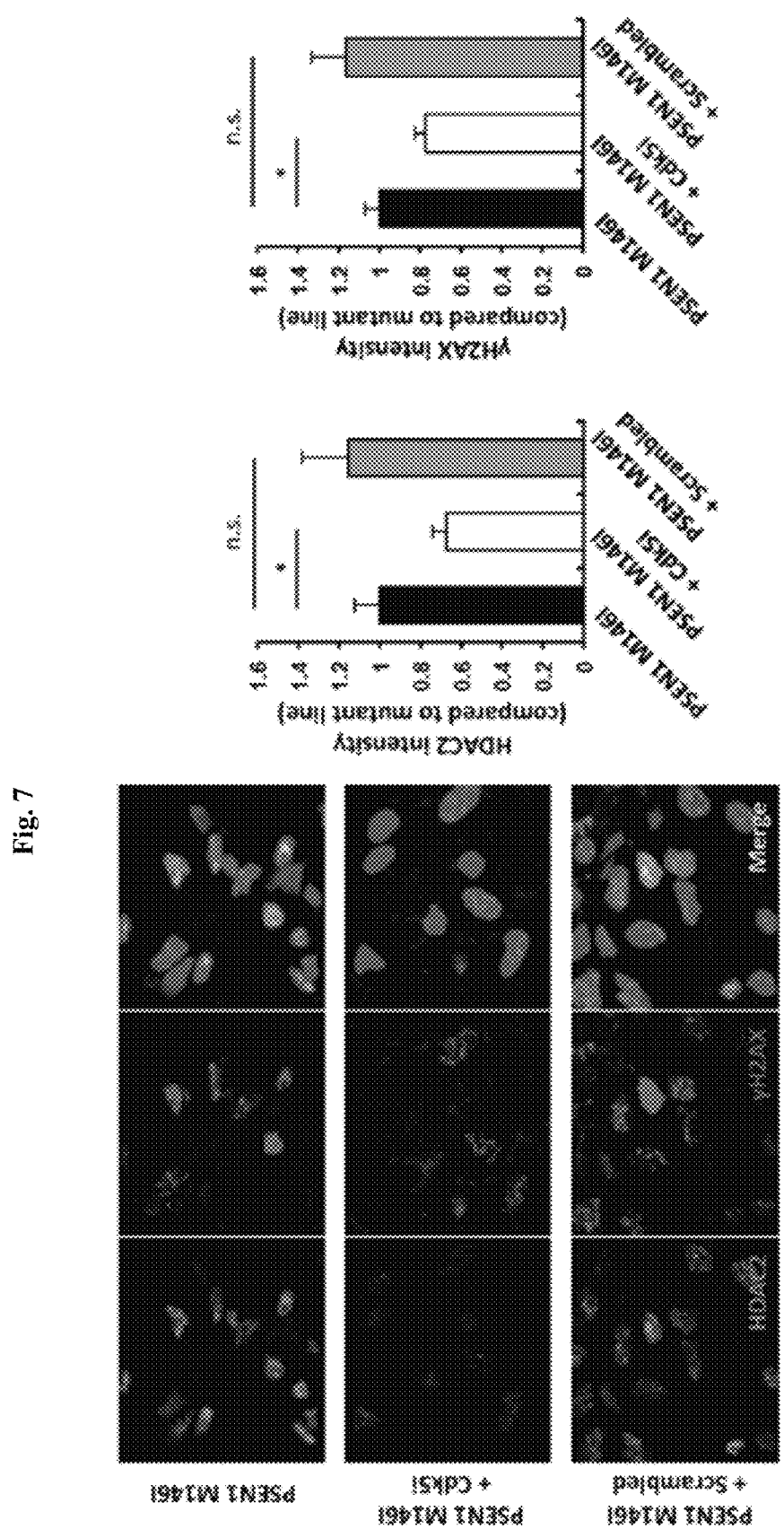
FIG. 7 shows neural progenitor cells (NPCs) treated with CDK5i peptide or its scrambled peptide; CDK5i significantly reduced levels of HDAC2 and βH2AX signals (indicative of DNA damage) while the scrambled protein did not show any effects.

NPCs were then treated with either CDK5i peptide or its scrambled peptide and the resulting pathological phenotypes were examined. CDK5i peptide was found to significantly reduce levels of HDAC2 and γH2AX (indicative of DNA damage) in PSEN 1 M146I NPCs, while the scrambled peptide did not show an effect (FIG. 7).

Example 3: CDK5i Peptide Inhibitors Having Functional Domains

An exemplary peptide having a CDK5 inhibitory domain and a functional domain (SEQ ID NO: 3) was designed (FIG. 9A). The functional domain enhances the delivery of Cdk5i peptide into cells. In the example it is a transactivator of transcription (TAT) peptide, a fragment of the HIV which was conjugated at the C-terminus to enable the Cdk5i peptide to translocate across cellular membrane. At the N-terminus, a fluorescein isothiocyanate (FITC) was conjugated with a linker (aminohexanoic acid; Ahx) for visualizing the distribution of the peptide.

Human iPSC-derived neural progenitor cells were treated with FITC-Ahx-Cdk5i-Tat (1 μM) (SEQ ID NO: 3) for 2 hr and subjected to imaging. The results are shown in FIG. 9B. The results show that FITC signals are in an intracellular location, demonstrating that the peptide is able to penetrate plasma membrane.

Example 4: Cdk5i Penetrates Blood Brain Barrier in Mice

Wild type mice were intraperitoneally injected with a single dose (40 mg/kg) of Cdk5i, and were sacrificed 24 hours after the injection. Prior to extracting the brain, mice were transcardially perfused with 40 mL of cold phosphobuffered saline (PBS) to ensure clearance of any Cdk5i circulating in the blood that may not have crossed the blood brain barrier. After the perfusion, the brains were dissected into two hemispheres and one hemisphere was lysed with cold lysis buffer (RIPA) to extract total protein. Total protein was then briefly run on a 12% acrylamide gel to separate large proteins and then digested with a trypsin enzyme and subjected to targeted mass spectrometry analysis using Cdk5i peptide sequence of SEQ ID NO. 3 linked to a GGG spacer/linker and FITC (Cdk5i sequence: FITC-GGG-SEQ ID NO. 3).

A substantial portion (11 amino acids out of 12) of the Cdk5i sequence including the conjugated tat protein sequence were detected using mass spectrometry based on the number of spectra and peak area. The data is shown in Table 1. Using targeted mass spectrometry, brain lysate from mice injected with Cdk5i show an enrichment for Cdk5i based on # of spectra and peak area ($2^{nd}$ row of data in Table 1).

TABLE 1

| Peptide | Mass | m/z | RT | Area | Scan | #Spec |
|---|---|---|---|---|---|---|
| R.CYSYGRK.K | 932.4174 | 467.216 | 9.49 | 6.13E+08 | 3964 | 12 |
| R.CYSYGR.K | 804.3224 | 403.1688 | 13.22 | 9.51E+09 | 5598 | 27 |
| G.ARAFGIPVR.C | 985.5821 | 493.7981 | 41.3 | 3.83E+07 | 18302 | 12 |
| R.AFGIPVRCYSYGRKK.R | 1800.946 | 601.3235 | 44.66 | 2.24E+06 | 19806 | 2 |
| R.AFGIPVRCYSYGRK.K | 1672.851 | 558.6249 | 53.56 | 3.75E+07 | 24210 | 5 |
| R.AFGIPVRCYSYGR.K | 1544.756 | 515.9263 | 63.95 | 8.42E+08 | 29189 | 22 |

The foregoing written specification is considered to be sufficient to enable one skilled in the art to practice the invention. The present invention is not to be limited in scope by examples provided, since the examples are intended as a single illustration of one aspect of the invention and other functionally equivalent embodiments are within the scope of the invention. Various modifications of the invention in addition to those shown and described herein will become apparent to those skilled in the art from the foregoing description and fall within the scope of the appended claims. The advantages of the invention are not necessarily encompassed by each embodiment of the invention.

What is claimed is:

1. A pharmaceutical composition, comprising a peptide of 12-50 amino acids in length having an amino acid sequence with greater than 96% identity to the amino acid sequence of SEQ ID NO: 1 having the following structure: ARAFGX$_1$PVRC X$_2$S* (X$_1$=I or V and X$_2$=Y or F), wherein the peptide is linked to a non-peptide molecule through a linker and a pharmaceutically acceptable carrier.

2. The pharmaceutical composition of claim 1, wherein the peptide comprises SEQ ID NO: 2.

3. The pharmaceutical composition of claim 1, wherein the peptide comprises at least one conservative substitution within the sequence of SEQ ID NO: 1.

4. The pharmaceutical composition of claim 1, wherein the pharmaceutically acceptable carrier comprises a polymer.

5. The pharmaceutical composition of claim 4, wherein the polymer comprises a hydrophilic block and an endosomolytic block.

6. The pharmaceutical composition of claim 5, wherein the hydrophilic block comprises polyethylene glycol methacrylate, and wherein the endosomolytic block comprises a diethylaminoethyl methacrylate-butyl methacrylate copolymer.

7. The pharmaceutical composition of claim 4, wherein the polymer is a stimuli-responsive polymer that responds to one or more stimuli selected from the group consisting of pH, temperature, UV-visible light, photo-irradiation, exposure to an electric field, ionic strength, and the concentration of certain chemicals by exhibiting a property change.

8. The pharmaceutical composition of claim 1, wherein the peptide comprises at least 1 additional amino acid at the N terminus of SEQ ID NO: 1.

9. The pharmaceutical composition of claim 1, wherein the peptide comprises at least 1 additional amino acid at the C terminus of SEQ ID NO: 1.

10. The pharmaceutical composition of claim 1, wherein the non-peptide molecule is a PEG or TEG.

11. A pharmaceutical composition, comprising a peptide of 12-50 amino acids in length having an amino acid sequence with at least 96% identity to the amino acid sequence of SEQ ID NO: 1 having the following structure: ARAFGX$_1$PVRC X$_2$S* (X$_1$=I or V and X$_2$=Y or F), wherein the peptide has a reinforced or stabilized secondary structure.

12. A pharmaceutical composition, comprising a peptide of 12-50 amino acids in length having an amino acid sequence with at least 96% identity to the amino acid sequence of SEQ ID NO: 1 having the following structure: ARAFGX$_1$PVRC X$_2$S* (X$_1$=I or V and X$_2$=Y or F), wherein the peptide is linked to a functional domain.

13. The pharmaceutical composition of claim 12, wherein the functional domain is a transactivation domain, a targeting domain or a stabilization domain.

14. The pharmaceutical composition of claim 13, wherein the transactivation domain is a transactivator of transcription (TAT) peptide.

15. The pharmaceutical composition of claim 13, wherein the transactivation domain is a peptide sequence of YGRKKRRQRRR (SEQ ID NO: 4).

16. A peptide consisting essentially of 12-25 amino acids in length having an amino acid sequence with at least 96% identity to the amino acid sequence of SEQ ID NO: 1 having the following structure: ARAFGX$_1$PVRC X$_2$S* (X$_1$=I or V and X$_2$=Y or F) and comprising at least one conservative substitution within the sequence.

* * * * *

SEQUENCE LISTING

```
<160> NUMBER OF SEQ ID NOS: 13

<210> SEQ ID NO 1
<211> LENGTH: 12
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (6)..(6)
<223> OTHER INFORMATION: X is Ile or Val
<220> FEATURE:
<221> NAME/KEY: MISC_FEATURE
<222> LOCATION: (11)..(11)
<223> OTHER INFORMATION: X is Tyr or Phe

<400> SEQUENCE: 1

Ala Arg Ala Phe Gly Xaa Pro Val Arg Cys Xaa Ser
1               5                   10

<210> SEQ ID NO 2
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 2

Ala Arg Ala Phe Gly Ile Pro Val Arg Cys Tyr Ser
1               5                   10

<210> SEQ ID NO 3
<211> LENGTH: 23
<212> TYPE: PRT
<213> ORGANISM: Artificial Sequence
<220> FEATURE:
<223> OTHER INFORMATION: Synthetic Polypeptide

<400> SEQUENCE: 3

Ala Arg Ala Phe Gly Ile Pro Val Arg Cys Tyr Ser Tyr Gly Arg Lys
1               5                   10                  15

Lys Arg Arg Gln Arg Arg Arg
            20

<210> SEQ ID NO 4
<211> LENGTH: 11
<212> TYPE: PRT
<213> ORGANISM: Artificial Sequence
```

-continued

```
<220> FEATURE:
<223> OTHER INFORMATION: Synthetic Polypeptide

<400> SEQUENCE: 4

Tyr Gly Arg Lys Lys Arg Arg Gln Arg Arg
1               5                   10

<210> SEQ ID NO 5
<211> LENGTH: 39
<212> TYPE: PRT
<213> ORGANISM: Homo sapiens

<400> SEQUENCE: 5

Asp Phe Gly Leu Ala Arg Ala Phe Gly Ile Pro Val Arg Cys Tyr Ser
1               5                   10                  15

Ala Glu Val Val Thr Leu Trp Tyr Arg Pro Pro Asp Val Leu Phe Gly
            20                  25                  30

Ala Lys Leu Tyr Ser Thr Ser
        35

<210> SEQ ID NO 6
<211> LENGTH: 39
<212> TYPE: PRT
<213> ORGANISM: Xenopus laevis

<400> SEQUENCE: 6

Asp Phe Gly Leu Ala Arg Ala Phe Gly Ile Pro Val Arg Cys Tyr Ser
1               5                   10                  15

Ala Glu Val Val Thr Leu Trp Tyr Arg Pro Pro Asp Val Leu Phe Gly
            20                  25                  30

Ala Lys Leu Tyr Ser Thr Ser
        35

<210> SEQ ID NO 7
<211> LENGTH: 38
<212> TYPE: PRT
<213> ORGANISM: Caenorhabditis elegans

<400> SEQUENCE: 7

Asp Phe Gly Leu Ala Arg Ala Phe Gly Val Pro Val Arg Cys Phe Ser
1               5                   10                  15

Ala Glu Val Val Thr Leu Trp Tyr Arg Pro Asp Val Leu Phe Gly Ala
            20                  25                  30

Lys Leu Tyr Asn Thr Ser
        35

<210> SEQ ID NO 8
<211> LENGTH: 39
<212> TYPE: PRT
<213> ORGANISM: Drosophila melanogaster

<400> SEQUENCE: 8

Asp Phe Gly Leu Ala Arg Ala Phe Gly Ile Pro Val Lys Cys Tyr Ser
1               5                   10                  15

Ala Glu Val Val Thr Leu Leu Tyr Arg Pro Pro Asp Val Leu Phe Gly
            20                  25                  30

Ala Lys Leu Tyr Thr Thr Ser
        35

<210> SEQ ID NO 9
<211> LENGTH: 39
```

<212> TYPE: PRT
<213> ORGANISM: Homo sapiens

<400> SEQUENCE: 9

Asp Phe Gly Leu Ala Arg Ala Phe Gly Val Pro Val Arg Thr Tyr Thr
1               5                   10                  15

His Glu Val Val Thr Leu Trp Tyr Arg Ala Pro Glu Ile Leu Leu Gly
            20                  25                  30

Cys Lys Tyr Tyr Ser Thr Ala
        35

<210> SEQ ID NO 10
<211> LENGTH: 39
<212> TYPE: PRT
<213> ORGANISM: Homo sapiens

<400> SEQUENCE: 10

Asp Phe Gly Leu Ala Arg Ala Phe Gly Ile Pro Ile Arg Val Tyr Thr
1               5                   10                  15

His Glu Val Val Thr Leu Trp Tyr Arg Ser Pro Glu Val Leu Leu Gly
            20                  25                  30

Ser Ala Arg Tyr Ser Thr Pro
        35

<210> SEQ ID NO 11
<211> LENGTH: 39
<212> TYPE: PRT
<213> ORGANISM: Homo sapiens

<400> SEQUENCE: 11

Asp Phe Gly Leu Ala Arg Ala Phe Gly Val Pro Leu Arg Thr Tyr Thr
1               5                   10                  15

His Glu Val Val Thr Leu Trp Tyr Arg Ala Pro Glu Ile Leu Leu Gly
            20                  25                  30

Ser Lys Phe Tyr Thr Thr Ala
        35

<210> SEQ ID NO 12
<211> LENGTH: 37
<212> TYPE: PRT
<213> ORGANISM: Homo sapiens

<400> SEQUENCE: 12

Asp Phe Gly Leu Ala Arg Ile Tyr Ser Tyr Gln Met Ala Leu Thr Pro
1               5                   10                  15

Val Val Val Thr Leu Trp Tyr Arg Ala Pro Glu Val Leu Leu Gln Ser
            20                  25                  30

Thr Tyr Ala Thr Pro
        35

<210> SEQ ID NO 13
<211> LENGTH: 37
<212> TYPE: PRT
<213> ORGANISM: Homo sapiens

<400> SEQUENCE: 13

Asp Phe Gly Leu Ala Arg Ile Tyr Ser Phe Gln Met Ala Leu Thr Ser
1               5                   10                  15

```
Val Val Val Thr Leu Trp Tyr Arg Ala Pro Glu Val Leu Leu Gln Ser
            20                  25                  30
Ser Tyr Ala Thr Pro
        35
```

UNITED STATES PATENT AND TRADEMARK OFFICE
CERTIFICATE OF CORRECTION

| | |
|---|---|
| PATENT NO. | : 12,384,818 B2 |
| APPLICATION NO. | : 16/119656 |
| DATED | : August 12, 2025 |
| INVENTOR(S) | : Li-Huei Tsai et al. |

Page 1 of 1

It is certified that error appears in the above-identified patent and that said Letters Patent is hereby corrected as shown below:

In the Specification

Column 1, Lines 11-15, GOVERNMENT SUPPORT section should read:
This invention was made with government support under NS051874 awarded by the National Institutes of Health. The government has certain rights in the invention.

Signed and Sealed this
Twenty-fifth Day of November, 2025

John A. Squires
*Director of the United States Patent and Trademark Office*